United States Patent
Correia De Matos Nolasco Lamas et al.

(10) Patent No.: US 10,684,206 B2
(45) Date of Patent: Jun. 16, 2020

(54) SYSTEMS AND RELATED METHODS OF IMAGING AND CLASSIFYING CELLS IN A BLOOD SAMPLE

(71) Applicant: BIOSURFIT S.A., Aveiro (PT)

(72) Inventors: Francisco Correia De Matos Nolasco Lamas, Lisbon (PT); João Manuel De Oliveira Garcia Da Fonseca, Azambuja (PT); André Do Rosário Magalhães, Lisbon (PT); José Pedro Santos Manso Côrte-Real, Lisbon (PT); Ricardo Manuel Marques Caleiro Cabeça, Lisbon (PT)

(73) Assignee: Biosurfit, S.A., Aveiro (PT)

( * ) Notice: Subject to any disclaimer, the term of this patent is extended or adjusted under 35 U.S.C. 154(b) by 150 days.

(21) Appl. No.: 15/515,529

(22) PCT Filed: Sep. 29, 2015

(86) PCT No.: PCT/EP2015/072392
§ 371 (c)(1),
(2) Date: Mar. 29, 2017

(87) PCT Pub. No.: WO2016/050755
PCT Pub. Date: Apr. 7, 2016

(65) Prior Publication Data
US 2017/0212028 A1  Jul. 27, 2017

(30) Foreign Application Priority Data

Sep. 29, 2014 (GB) .................................. 1417178.9
Sep. 29, 2014 (PT) ......................................... 107931

(51) Int. Cl.
*G06K 9/00* (2006.01)
*G01N 15/02* (2006.01)
(Continued)

(52) U.S. Cl.
CPC ..... *G01N 15/0266* (2013.01); *G01N 15/0227* (2013.01); *G01N 15/147* (2013.01);
(Continued)

(58) Field of Classification Search
CPC ......... G06T 7/0012; G06T 2207/10016; G06T 2207/10056; G06T 2207/30101;
(Continued)

(56) References Cited

U.S. PATENT DOCUMENTS 4,075,462 A    2/1978   Rowe
5,760,950 A *  6/1998   Maly .................. G02B 21/0028
                                                                    359/368
(Continued)

FOREIGN PATENT DOCUMENTS

EP    1699016 A2    9/2006
EP    2130174 B1    9/2010
(Continued)

OTHER PUBLICATIONS

PCT International Search Report Opinion for PCT/EP2105/072392, dated Apr. 4, 2016, 5 pgs.
(Continued)

*Primary Examiner* — Guillermo M Rivera-Martinez
(74) *Attorney, Agent, or Firm* — Patterson Thuente Pedersen, P.A.

(57) ABSTRACT

Systems and methods for classifying blood cells in a blood sample are disclosed. A series of frames of the blood sample as it flows through a field of view of an image capture device are captured and analysed. Advantageously, the disclosed systems and methods combine the availability of morphological cell data with the convenience of a flow-through arrangement. The classification results can be used for estimating cell counts in a blood sample.

22 Claims, 15 Drawing Sheets

(51) Int. Cl.

| | |
|---|---|
| *G01N 15/14* | (2006.01) |
| *G06K 9/62* | (2006.01) |
| *G01N 33/49* | (2006.01) |
| *G01N 15/10* | (2006.01) |
| *G01N 35/00* | (2006.01) |
| *B01L 3/00* | (2006.01) |

(52) U.S. Cl.
CPC ..... *G01N 15/1436* (2013.01); *G01N 33/4915* (2013.01); *G06K 9/00134* (2013.01); *G06K 9/00147* (2013.01); *G06K 9/629* (2013.01); *B01L 3/502761* (2013.01); *G01N 15/1475* (2013.01); *G01N 15/1484* (2013.01); *G01N 2015/1006* (2013.01); *G01N 2015/1087* (2013.01); *G01N 2015/1486* (2013.01); *G01N 2015/1488* (2013.01); *G01N 2035/00158* (2013.01)

(58) Field of Classification Search
CPC ............ G06T 2207/30242; G06T 7/20; G06T 2207/30104; G06T 7/136; G02B 21/365; G02B 21/002; G06K 9/00147
See application file for complete search history.

(56) References Cited

U.S. PATENT DOCUMENTS

| | | | |
|---|---|---|---|
| 5,880,835 A | 3/1999 | Yamazaki et al. | |
| 7,295,309 B1 | 11/2007 | Morrison | |
| 8,426,122 B2 | 4/2013 | Parikh | |
| 2002/0093641 A1 | 7/2002 | Ortyn | |
| 2004/0067544 A1* | 4/2004 | Vogel | C07K 14/245 435/7.32 |
| 2004/0168982 A1* | 9/2004 | Bitensky | B01L 3/5027 210/649 |
| 2004/0223135 A1* | 11/2004 | Ortyn | G01N 15/1012 356/28 |
| 2006/0024756 A1* | 2/2006 | Tibbe | G01N 15/1463 435/7.2 |
| 2006/0117077 A1* | 6/2006 | Kiiveri | G06F 19/24 708/200 |
| 2010/0169811 A1* | 7/2010 | Yamada | G01N 15/1475 715/764 |
| 2011/0131028 A1* | 6/2011 | Hodgkin | G06F 19/12 703/11 |
| 2013/0177973 A1 | 7/2013 | Kondo | |
| 2013/0185097 A1* | 7/2013 | Saria | G06Q 10/00 705/3 |
| 2014/0002617 A1 | 1/2014 | Zhang | |
| 2014/0012104 A1* | 1/2014 | Chen | A61B 5/1455 600/322 |
| 2014/0152801 A1* | 6/2014 | Fine | G02B 21/0008 348/79 |
| 2014/0273076 A1* | 9/2014 | Adams | G01N 33/5094 435/39 |
| 2015/0153367 A1* | 6/2015 | Yoshida | B01L 3/5027 435/29 |
| 2015/0204771 A1* | 7/2015 | Sun | G06T 7/0012 382/134 |
| 2015/0302237 A1* | 10/2015 | Ohya | G06K 9/00147 382/133 |
| 2017/0209864 A1* | 7/2017 | Grisham | B01L 3/502746 |

FOREIGN PATENT DOCUMENTS

| | | |
|---|---|---|
| EP | 2188760 B1 | 10/2011 |
| WO | WO 2013/135713 A1 | 9/2013 |
| WO | WO 2014/146061 A1 | 9/2014 |

OTHER PUBLICATIONS

PCT Written Opinion of the ISA for PCT/EP2105/072392, dated Apr. 4, 2016, 11 pgs.
PCT IPRP for PCT/EP2105/072392, dated Apr. 4, 2016, 12 pgs.
Portuguese Search Report for Portuguese Application No. 107931, dated Feb. 23, 2015, 10 pgs.
Saraswat, M., Arya, K.V.—"Automated microscopic image analysis for leukocytes identification: A survey", Micron, Apr. 12, 2014 [online], vol. 65, p. 20-33.
Nazlibilek, S., et al.—"Automatic segmentation, counting, size determination and classification of white blood cells", Measurement, May 2, 2014 [online], vol. 55, p. 58-65.
Mukherjee, D. P., Acton, S. T.—"Level Set Analysis for Leukocyte Detection and Tracking", IEEE Transactions on Image Processing, vol. 13, No. 4, Apr. 2004, p. 562-572.
S.B. Kotsiantis, "Supervised Machine Learning: A Review of Classification Techniques", Informatica, vol. 31, No. 3, Oct. 2007, pp. 249-268.
Congcong Zhang et al, "White Blood Cell Segmentation by Color-Space-Based K-Means Clustering", Sensors 2014, 14, 16128-16147.
Herbert Ramoser et al, doi:10.3390/s140916128; "Leukocyte segmentation and classification in blood-smear images", Proceedings of the 2005 IEEE Engineering in Medicine and Biology 27th Annual Conference, Shanghai, China, Sep. 1-4, 2005.
N. Landwehr, M. Hall and E. Frank, "Logistic Model Trees", Machine Learning, vol. 59, pp. 161-205, 2005.
http://weka.sourceforge.net/doc.dev/weka/classifiers/functions/SimpleLogistic.html, SimpleLogistic, 12 pages.
http://www.cs.waikato.ac.nz/ml/weka/, Weka 3: Data Mining Software in Java,1 page.
Examination Report with Search results for corresponding EP application No. 15 770 923.9-1001, dated May 14, 2018, 10 pages.
Office Action for corresponding U.S. Appl. No. 15/940,330, dated Jul. 10, 2018, 3 pages.
Class Simple Logistic, http://weka.sourceforge.net/doc.dev/weka/classifiers/functions/SimpleLogistic.html, printed out on Jul. 29, 2019, 12 pages.
Weka 3: Machine Learning Software in Java, https://www.cs.waikato.ac.nz/ml/weka/, printed on Jul. 29, 2019, 1 page.

* cited by examiner

| Object parameters |
|---|
| Cytoplasm mean of Hue channel |
| Cytoplasm standard deviation of Hue channel |
| Area of cytoplasm |
| Perimeter of cytoplasm |
| Form factor of cytoplasm (relates to the shape of the cytoplasm) |
| Compactness of cytoplasm (relates to the shape of the cytoplasm) |
| Convex hull of cytoplasm (relates to convexity of the cytoplasm) |
| Cytoplasm mean of Saturation channel |
| Cytoplasm standard deviation of Saturation channel |
| Cytoplasm mean of value channel |
| Standard deviation of value channel |
| Cytoplasm2 mean of hue channel |
| Cytoplasm2 standard deviation of hue channel |
| Area of cytoplasm2 |
| Perimeter of cytoplasm2 |
| Form factor of cytoplasm2 () |
| Compactness of cytoplasm2 () |
| Convex hull of cytoplasm2 |
| Cytoplasm2 mean of Saturation channel |
| Cytoplasm2 standard deviation of Saturation channel |
| Cytoplasm2 mean of Value channel |
| Cytoplasm2 standard deviation of Value channel |
| Nucleus mean of Hue channel |
| Nucleus standard deviation of Hue channel |
| Area of nucleus |
| Perimeter of nucleus |
| Form factor of nucleus () |
| Compactness of nucleus |
| Convex hull of nucleus |
| Nucleus mean of Saturation channel |
| Nucleus standard deviation of Saturation channel |
| Nucleus mean of Value channel |
| Nucleus standard deviation of Value channel |
| Total cell area |
| Total cell perimeter |
| Cell form factor |
| Cell compactness |
| Cell focus metric (relates to focus quality of frame which in turn is linked with cell characteristics) |
| Number of nuclei in the cell |

Fig. 4

|            | Frame 1 | Frame 2 | Frame 3 | - - - - |
|------------|---------|---------|---------|---------|
| Lymphocyte | 90%     | 85%     | 5%      | - - - - |
| Monocyte   | 5%      | 12%     | 90%     | - - - - |
| Eosenophil | 1%      | 1%      | 2%      | - - - - |
| ⋮          | ⋮       | ⋮       | ⋮       |         |

| Object parameters |
|---|
| Cytoplasm mean of Hue channel |
| Cytoplasm standard deviation of Hue channel |
| Area of cytoplasm |
| Perimeter of cytoplasm |
| Form factor of cytoplasm (relates to the shape of the cytoplasm) |
| Compactness of cytoplasm (relates to the shape of the cytoplasm) |
| Convex hull of cytoplasm (relates to convexity of the cytoplasm) |
| Cytoplasm mean of Saturation channel |
| Cytoplasm standard deviation of Saturation channel |
| Cytoplasm mean of value channel |
| Standard deviation of value channel |
| Cytoplasm2 mean of hue channel |
| Cytoplasm2 standard deviation of hue channel |
| Area of cytoplasm2 |
| Perimeter of cytoplasm2 |
| Form factor of cytoplasm2 () |
| Compactness of cytoplasm2 () |
| Convex hull of cytoplasm2 |
| Cytoplasm2 mean of Saturation channel |
| Cytoplasm2 standard deviation of Saturation channel |
| Cytoplasm2 mean of Value channel |
| Cytoplasm2 standard deviation of Value channel |
| Nucleus mean of Hue channel |
| Nucleus standard deviation of Hue channel |
| Area of nucleus |
| Perimeter of nucleus |
| Form factor of nucleus () |
| Compactness of nucleus |
| Convex hull of nucleus |
| Nucleus mean of Saturation channel |
| Nucleus standard deviation of Saturation channel |
| Nucleus mean of Value channel |
| Nucleus standard deviation of Value channel |
| Total cell area |
| Total cell perimeter |
| Cell form factor |
| Cell compactness |
| Cell focus metric (relates to focus quality of frame which in turn is linked with cell characteristics) |
| Number of nuclei in the cell |

Fig. 19

SYSTEMS AND RELATED METHODS OF IMAGING AND CLASSIFYING CELLS IN A BLOOD SAMPLE

RELATED APPLICATIONS

This application is a National Phase entry of PCT Application No. PCT/EP2015/072392, filed Sep. 29, 2015, which claims priority from Great Britain Application No. 1417178.9, filed Sep. 29, 2014, and which claims priority from Portuguese Application No. 107931 T, filed Sep. 29, 2014, the disclosures of which are hereby incorporated by referenced herein in their entirety.

FIELD OF THE INVENTION

The present invention relates to the counting of cells in a blood sample.

BACKGROUND OF THE INVENTION

The counting of cells in a blood sample is an important diagnostic tool.

An example of a known approach to counting cells in a blood sample is flow cytometry. In flow cytometry, a blood sample flows through a capillary such that cells pass one by one in front of a light source and detection arrangement. The reflected and/or transmitted light is detected and analysed. The characteristics of the detected light depend on characteristics of the cells in the sample and how they are stained and, in this way, cells are classified and counted. However, no morphological information for the cells is obtained using flow cytometry. Morphological analysis can be carried out on a blood sample by sandwiching the sample between two slides and investigating the sample under a microscope. Automated systems for cell counting are known which use cartridges of pre-prepared slides. Such slides need to be prepared manually for each sample to be analysed. This is a time-consuming process, in spite of the partial automation.

It would be desirable to have a system for cell counting in which the morphological information of cells is not lost but instead is used to improve the accuracy of the cell counting process and which, further, does not require the preparation of slides.

SUMMARY OF THE INVENTION

Aspects of the invention are set out in the independent claims. Further, optional, features of the invention are set out in the dependent claims.

In some embodiments, there is provided a method of classifying blood cells in a blood sample. The method comprises the following:
 capturing a sequence of frames of the sample with an image capture device as the sample flows through a field of view of the image capture device;
 segmenting each frame into objects and background;
 tracking each segmented object over at least some of the frames;
 classifying the tracked objects in each of the respective at least some of the frames to obtain a classification result for each tracked object and each of the respective at least some of the frames; and
 computing an overall classification result for each tracked object based on the respective classification results from each of the at least some of the frames to classify each tracked object as one of a plurality of object types, wherein the object types include one or more cell types.

In some embodiments, there is provided a system for classifying blood cells in a blood sample, the system comprising an image capture device having a field of view and an image processor. The image processor is configured to implement the above method.

Advantageously, the accuracy of the cell counting is improved by obtaining a classification result for an object in more than one captured frame. In doing so, multiple independent observations are obtained as the sample flows across the field of view and each object may be viewed from different angles, creating a rich set of morphological data. As compared to cell cytometry, morphological information is not lost and as compared to known morphological methods, manual slide preparation is not required.

In some embodiments, the classification results for each tracked object and each of the respective frames may be obtained using a Simple Logistic Model. In other embodiments, other classifiers, as will be known to a person skilled in the relevant field, may be used. For examples, refer to S. B. Kotsiantis, 'Supervised Machine Learning: A Review of Classification Techniques', Informatica, vol. 31, number 3, October 2007, pages 249-268.

In some embodiments, computing an overall classification result includes averaging or calculating the median of the respective classification results over frames. In other embodiments computing an overall classification result includes applying one or more rules to the classification results from each of the individual frames in which the object is tracked. This allows any classification results from each frame that would be lost in the process of averaging to be considered in determining the overall classification process. For example, setting such rules allows any distinguishing characteristics of a certain object type that are detected in one or more of the frames to be considered in the overall classification of an object even if it is only detected in a relatively small number of frames. For example, this can improve detections of cells which have a highly characteristic configuration of the nucleus only when viewed from some directions.

In some embodiments, the classification result for each tracked object for each frame in which that object is tracked includes a set of class belonging scores of that object belonging to each of the object types (e.g. a set of class belonging likelihoods or probabilities) or a classification, that is a binary indication of class belonging, or an identifier of an assigned object type. Likewise, the overall classification result may be a set of class belonging scores of that object belonging to each of the object types (e.g. a set of class belonging likelihoods or probabilities) or a classification, that is a binary indication of class belonging or an assigned object type. The set of class-belonging scores may be used in further computations.

In other embodiments, in obtaining the overall classification result for a given object, each individual frame in which that object appears gives a vote. The overall classification is then obtained based on these votes. In some embodiments, the object is classified as the object type with the most votes. In other embodiments, one or more rules are implemented such that the votes from the remaining frames can be overridden by a predetermined number of votes for a predetermined selection of object types. In some embodiments, the number of votes for each object type is taken into account in classifying the object overall but one or more rules, as outlined above, are also implemented.

The classification result for each tracked object and frame may be calculated prior to tracking, for all objects in the at least some frames, so that the (frame by frame) classification results are immediately available once an object has been tracked. Alternatively, (frame by frame) classification results may be calculated after tracking, in which case they may be calculated only for tracked objects and only in those respective frames in which each tracked object was tracked.

In some embodiments, an object type has a non-isotropic characteristic feature and the method includes assigning a tracked object to that object type if the class belonging score for that object belonging to that object type exceeds a threshold value for one or more frames. This allows an 'override' of the other classification results from each of the other frames if, for one or more frames, the class-belonging score for the object for a given object type is sufficiently high. In other embodiments where an object type has a non-isotropic feature, the method includes assigning a tracked object to that object type if a change in the class-belonging score for that object type between two frames exceeds a threshold value. This means that if there is a large enough 'jump' in the score for an object for a given object type, then the object is classified as belonging to that object type. If the classification results for each frame were averaged then this information may be lost.

As mentioned above, the object types include one or more cell types. In some embodiments, these cell types are leukocytes (white blood cells). In some embodiments, these cell types include neutrophils, basophils, eosinophils, lymphocytes and monocytes. In some embodiments, the method comprises computing the proportion of the number of objects classified as each cell type out of the total number of objects classified as any one of the cell types. These proportions are known as the differential cell counts. In some embodiments, the object types also include non-leukocyte types, such as red blood cells, red blood cell fragments, cell aggregates etc.

In some embodiments, the method comprises estimating an absolute count of objects (objects per unit volume of sample) belonging to any one of the leukocyte types. This is then used to compute an absolute count of objects belonging to each of the leukocyte types based on the estimate of the total count of objects belonging to any one of the leukocyte types and the proportions of the number of objects belonging to each leukocyte type.

In some embodiments, estimating the absolute count of leukocytes includes identifying objects belonging to any one of the leukocyte types in each frame. A plurality of frames is selected and a count of these identified leukocytes in each selected frame is determined. These frame counts are then combined to compute an estimated total count of leukocytes belonging to any one of the leukocyte types.

In some embodiments, an absolute cell count is estimated as follows, by:
  selecting a plurality of frames,
  counting the number of cells within each of the selected frames and
  combining these counts to compute an estimated cell count.

Combining the counts may comprise fitting a distribution function to the frame cell counts and computing an estimated cell count based on the fitted distribution. The estimated cell count may be derived using one or more parameters of the fitted distribution. The fitted distribution may be a Gamma or a Poisson distribution.

Computing the estimated cell count may involve splitting the sequence of frames into subset blocks and computing a respective estimated cell count by fitting a respective distribution to each block. One of the estimated respective cell counts can then be used as the result to be stored (or returned) by making a selection based on one or more of the position of the subset block in the sequence, the magnitude of the respective estimated counts and a goodness of fit indicator. In some embodiments, if the goodness of fit indicator for any block is not good enough, i.e. if it is lower than a predetermined threshold, then the respective estimated cell count for that block is discarded.

Alternatively, combining the frame cell counts may include computing a mean or median of the frame cell counts.

In alternative embodiments, frames are selected based on an estimate of cell velocity. By considering cell velocity, the next frame in the subset of selected frames can be selected such that the objects in the previous frame are likely to have left the field of view. Doing so may involve computing the number of frames needed before the objects in the previous frame are likely to have left the field of view. This may reduce the chances of double counting.

In both types of embodiments (distribution fitting, speed-based selection), the selecting of frames may include setting a cut-off position, wherein frames with a position in the sequence of frames that make up the video that is beyond the cut-off position are not selected.

In some embodiments, an absolute cell count may be estimated based on an estimated cell count and the volume of sample contained within the field of view of the image capture device. In some embodiments, the volume of sample contained within the field of view may be corrected for any obstructions to the flow that are found within the field of view. This may be done by first detecting an obstruction and then estimating its volume. The estimated volume of the obstruction may then be subtracted from the unobstructed volume associated with the field of view. Detecting an obstructed area may include partitioning the field of view into candidate areas and marking a candidate area as obstructed if less than a threshold amount of cells have been identified over the sequence of frames in that candidate area.

In some embodiments, there is provided a system for estimating a cell count in a blood sample wherein the system comprises an image capture device having a field of view and an image processor, wherein the image processor is configured to carry out any or all of the method steps as described above or any combination thereof.

In some embodiments there is provided a device for use with the above-described system for estimating a cell count in a blood sample. The device comprises a microfluidic liquid handling structure, comprising a loading chamber having an inlet port, a connection conduit and a waste chamber. The loading chamber is connected to the waste chamber via the connection conduit. The connection conduit comprises a preparation portion and a detection portion. The preparation portion contains one or more reagents which, when the device is in operation, react with the sample to cause the lysing of red blood cells and differential staining of the white blood cells. In some embodiments, these reagents may be provided in the preparation portion in dry form, for re-suspension by the sample. Alternatively, in some embodiments, the reagents may be held in another region of the microfluidic liquid handling structure, but still such that the lysing and staining of the sample occurs before it enters the field of view of the image capture device. In other embodiments, the sample may be mixed with reagents outside of the microfluidic liquid handling structure, before being introduced into the microfluidic liquid handling structure.

The detection portion is configured to enable the sample to be imaged by the image capture device when the system is in operation. In some embodiments, the detection portion has a depth normal to the field of view of the image capture device to constrain the sample in the field of view within the depth of field of the image capture device. The depth of the detection portion may be less than 0.030 mm or less than 0.020 mm. In some embodiments, the detection portion is at least as wide as it is deep.

The above means that the depth of the detection portion is such that all cells flowing through the detection portion can be imaged by the image capture device. This will be the case where the depth is of the order of white blood cell sizes, for example less than twice the largest cell dimension.

As mentioned above, cell velocities may be estimated by tracking cells from one frame to the next. In some embodiments, additionally or alternatively, the dimensions and configuration of the microfluidic liquid handling structure can be designed such that the rate of flow of sample through the detection portion can be considered substantially constant after a certain period of time has elapsed since the blood sample first reaches the detection portion, for example three seconds. This constant flow rate is then, in some embodiments, taken to be the velocity of objects in the sample, for example cells.

In some embodiments, the device may comprise a cartridge providing the microfluidic liquid handling device, configured to be inserted into a holding structure for holding the cartridge relative to the image capture device. In some embodiments, the cartridge may be substantially disk shaped and in some embodiments, the cartridge may be arranged for rotation about an axis of rotation, the axis of rotation being defined by a feature of the device for engaging a drive mechanism for rotating the device. In some embodiments, the cartridge is rotated about the axis of rotation for processing the same or a different sample in another portion of the cartridge.

In some embodiments, the image capture device may be positioned above the detection portion of the connection conduit and in other embodiments it may be positioned below the detection portion.

In operation, a sample is introduced into the microfluidic liquid handling structure via the inlet port and the sample flows into the loading chamber. The sample is then drawn into the connection conduit by capillarity and flows through the conduit under the action of capillary forces. In some embodiments, flow of the sample through the microfluidic liquid handling structure may be driven by pressure differences or by any other means as will be well known to a person skilled in the relevant field.

As mentioned above, the sample may react with lysing and staining agents before entering the field of view of the image capture device. When the sample enters the field of view, the image capture device begins capturing frames of the sample which together form a video. In some embodiments, the rate at which frames are taken can be adapted according to the parameters of a specific assay, for example based on the rate of flow of the sample across the field of view. Additionally or alternatively, the total number of frames taken can be adapted to the parameters of the assay.

Once the frames of the sample have been captured, the image processor carries out a number of processing steps on the frames, as outlined above. In some embodiments, the frames are segmented into objects and background and the segmented objects are tracked over as many frames as possible. In some embodiments, this tracking is based on the assumption that an object in a first frame is that same object as the object in the next frame with the position closest to that of the object in the first frame. In some embodiments, an object is only tracked from a first frame to the next if there are no objects within a predetermined 'safe-distance' from the object in the second frame.

In a further aspect of the invention, there is provided a computer readable medium or computer readable media storing coded instructions that, when executed on a processor, implement any or all of the method steps as described above or any combination thereof. This computer readable medium or media can comprise any kind of data storage medium, for example one or more of a magnetic or optical disc, a hard disc, solid state or other data storage device, including RAM, ROM, EPROM, EEPROM or Flash.

In yet a further aspect of the invention there is provided a method of obtaining a blood cell count, the method comprising imaging a blood sample as it flows past an image capture device to capture a sequence of frames; segmenting each frame into objects and background; classifying the objects in each frame as belonging to one of a plurality of object types, wherein the object types include one or more cell types; and obtaining a blood cell count based on the classification, wherein obtaining a blood cell count includes counting those objects that have been classified as belonging to one of the one or more cell types.

The cells may be counted to obtain differential or absolute counts in accordance with the aspects and embodiments set out above.

Aspects of the invention also extend to a system comprising an image capture device and a processor configured to implement such a method in accordance with this yet further aspect. Any of the method steps described may, in some embodiments, be carried out by or under the control of a processor.

Aspects of the invention further extend to image segmentation methods as set out in the various embodiments of segmentation methods set out below, as well as to systems comprising means for implementing such methods, for example systems comprising a processor configured to implement such methods and also extends to computer program products and computer readable media with coded instruction for implementing such methods.

While most of the description is made in terms of classifying white blood cells (leukocytes) and more specifically cell types corresponding to different healthy leukocyte populations, the invention is not so limited and other cell types can be classified and counted, for example diseased or cancerous white blood cells or red blood cells.

In some embodiments, there is provided a method of estimating a cell count in a blood sample. The method comprises capturing a sequence of frames of the sample with an image capture device as the sample flows through a field of view of the image capture device, identifying cells in each frame, selecting a plurality of frames of the sequence of frames, determining a frame cell count of identified cells in each selected frame and combining the determined frame cell counts to compute an estimated cell count.

In some embodiments, identifying cells in each frame includes classifying objects in each frame. Parameters of each object are extracted from the frame and, in some embodiments, the classification result for each object may be obtained using a Simple Logistic Model. In other embodiments, other classifiers, as will be known to a person skilled in the relevant field, may be used. For examples, refer to S. B. Kotsiantis, 'Supervised Machine Learning: A Review of Classification Techniques', Informatica, vol. 31, number 3, October 2007, pages 249-268. Once each object in a frame has been classified, the number of cells within the frame is counted. As such, a frame cell count is found for each frame.

In some embodiments, combining the counts may comprise fitting a distribution function to the frame cell counts and computing an estimated cell count based on the fitted distribution. The estimated cell count may be derived using one or more parameters of the fitted distribution. The fitted distribution may be a Gamma or a Poisson distribution.

Computing the estimated cell count may, in some embodiments, involve splitting the sequence of frames into subset blocks and computing a respective estimated cell count by fitting a respective distribution to each block. One of the estimated respective cell counts can then be used as the result to be stored (or returned) by making a selection based on one or more of the position of the subset block in the sequence, the magnitude of the respective estimated counts and a goodness of fit indicator. In some embodiments, if the goodness of fit indicator for any block is not good enough, i.e. if it is lower than a predetermined threshold, then the respective estimated cell count for that block is discarded.

Alternatively, combining the frame cell counts may include computing a mean or median of the frame cell counts.

In alternative embodiments, frames are selected based on an estimate of cell velocity. By considering cell velocity, the next frame in the subset of selected frames can be selected such that the objects in the previous frame are likely to have left the field of view. Doing so may involve computing the number of frames needed before the objects in the previous frame are likely to have left the field of view. This may reduce the chances of double counting.

In some embodiments, cell velocities are estimated by tracking objects from one frame to the next. This process, along with alternative methods of estimating cell velocities, will be described below.

In both types of embodiments (distribution fitting, speed-based selection), the selecting of frames may include setting a cut-off position, wherein frames with a position in the sequence of frames that make up the video that is beyond the cut-off position are not selected.

In some embodiments, an absolute cell count may be estimated based on an estimated cell count and the volume of sample contained within the field of view of the image capture device. In some embodiments, the volume of sample contained within the field of view may be corrected for any obstructions to the flow that are found within the field of view. This may be done by first detecting an obstruction and then estimating its volume. The estimated volume of the obstruction may then be subtracted from the unobstructed volume associated with the field of view. Detecting an obstructed area may include partitioning the field of view into candidate areas and marking a candidate area as obstructed if less than a threshold amount of cells have been identified over the sequence of frames in that candidate area.

In some embodiments, there is provided a system for estimating a cell count in a blood sample wherein the system comprises an image capture device having a field of view and an image processor, wherein the image processor is configured to carry out any or all of the method steps as described above or any combination thereof.

In some embodiments there is provided a device for use with the above-described system for estimating a cell count in a blood sample. The device comprises a microfluidic liquid handling structure, comprising a loading chamber having an inlet port, a connection conduit and a waste chamber. The loading chamber is connected to the waste chamber via the connection conduit. The connection conduit comprises a preparation portion and a detection portion. The preparation portion contains one or more reagents which, when the device is in operation, react with the sample to cause the lysing of red blood cells and differential staining of the white blood cells. In some embodiments, these reagents may be provided in the preparation portion in dry form, for resuspension by the sample. Alternatively, in some embodiments, the reagents may be held in another region of the microfluidic liquid handling structure, but still such that the lysing and staining of the sample occurs before it enters the field of view of the image capture device. In other embodiments, the sample may be mixed with reagents outside of the microfluidic liquid handling structure, before being introduced into the microfluidic liquid handling structure.

The detection portion is configured to enable the sample to be imaged by the image capture device when the system is in operation. In some embodiments, the detection portion has a depth normal to the field of view of the image capture device to constrain the sample in the field of view within the depth of field of the image capture device. The depth of the detection portion may be less than 0.030 mm or less than 0.020 mm. In some embodiments, the detection portion is at least as wide as it is deep.

The above means that the depth of the detection portion is such that all cells flowing through the detection portion can be imaged by the image capture device. This will be the case where the depth is of the order of white blood cell sizes, for example less than twice the largest cell dimension.

As mentioned above, cell velocities may be estimated by tracking cells from one frame to the next. In some embodiments, additionally or alternatively, the dimensions and configuration of the microfluidic liquid handling structure can be designed such that the rate of flow of sample through the detection portion can be considered substantially constant after a certain period of time has elapsed since the blood sample first reaches the detection portion, for example three seconds. This constant flow rate is then, in some embodiments, taken to be the velocity of objects in the sample, for example cells.

In some embodiments, the device may comprise a cartridge providing the microfluidic liquid handling device, configured to be inserted into a holding structure for holding the cartridge relative to the image capture device. In some embodiments, the cartridge may be substantially disk shaped and in some embodiments, the cartridge may be arranged for rotation about an axis of rotation, the axis of rotation being defined by a feature of the device for engaging a drive mechanism for rotating the device. In some embodiments, the cartridge is rotated about the axis of rotation for processing the same or a different sample in another portion of the cartridge.

In some embodiments, the image capture device may be positioned above the detection portion of the connection conduit and in other embodiments it may be positioned below the detection portion.

In operation, a sample is introduced into the microfluidic liquid handling structure via the inlet port and the sample flows into the loading chamber. The sample is then drawn into the connection conduit by capillarity and flows through the conduit under the action of capillary forces. In some embodiments, flow of the sample through the microfluidic liquid handling structure may be driven by pressure differences or by any other means as will be well known to a person skilled in the relevant field.

As mentioned above, the sample may react with lysing and staining agents before entering the field of view of the image capture device. When the sample enters the field of view, the image capture device begins capturing frames of the sample which together form a video. In some embodiments, the rate at which frames are taken can be adapted according to the parameters of a specific assay, for example based on the rate of flow of the sample across the field of view. Additionally or alternatively, the total number of frames taken can be adapted to the parameters of the assay.

Once the frames of the sample have been captured, the image processor carries out a number of processing steps on the frames, as outlined above. In some embodiments, the frames are segmented into objects and background and the segmented objects are tracked over as many frames as possible. In some embodiments, this tracking is based on the assumption that an object in a first frame is that same object as the object in the next frame with the position closest to that of the object in the first frame. In some embodiments, an object is only tracked from a first frame to the next if there are no objects within a predetermined 'safe-distance' from the object in the second frame.

In a further aspect of the invention, there is provided a computer readable medium or computer readable media storing coded instructions that, when executed on a processor, implement any or all of the method steps as described above or any combination thereof. This computer readable medium or media can comprise any kind of data storage medium, for example one or more of a magnetic or optical disc, a hard disc, solid state or other data storage device, including RAM, ROM, EPROM, EEPROM or Flash.

In yet a further aspect of the invention there is provided a method of obtaining a blood cell count, the method comprising imaging a blood sample as it flows past an image capture device to capture a sequence of frames; segmenting each frame into objects and background; classifying the objects in each frame as belonging to one of a plurality of object types, wherein the object types include one or more cell types; and obtaining a blood cell count based on the classification, wherein obtaining a blood cell count includes counting those objects that have been classified as belonging to one of the one or more cell types.

The cells may be counted to obtain an absolute count in accordance with the aspects and embodiments set out above. The absolute count of white blood cells is the estimated number of white blood cells per unit volume of blood.

Aspects of the invention also extend to a system comprising an image capture device and a processor configured to implement such a method in accordance with this yet further aspect. Any of the method steps described may, in some embodiments, be carried out by or under the control of a processor.

Aspects of the invention further extend to image segmentation methods as set out in the various embodiments of segmentation methods set out below, as well as to systems comprising means for implementing such methods, for example systems comprising a processor configured to implement such methods and also extends to computer program products and computer readable media with coded instruction for implementing such methods.

While most of the description is made in terms of classifying white blood cells (leukocytes) and more specifically cell types corresponding to different healthy leukocyte populations, the invention is not so limited and other cell types can be classified and counted, for example diseased or cancerous white blood cells or red blood cells.

BRIEF DESCRIPTION OF THE DRAWINGS

Embodiments are now described in detail by way of example, with reference to the accompanying drawings, in which:

FIG. 4 provides a list of object parameters that may be used in classifying objects;

FIG. 19 provides a list of object parameters that may be used in classifying objects;

The figures are not to scale and further, are not drawn in exact proportion for the purpose of clarity.

DETAILED DESCRIPTION OF THE INVENTION

Part I
Overview

In this disclosure, four main processes are described which are used to obtain one of two types of white blood cell count by acquiring video frames of a sample being imaged as it flows. These two types are: differential white blood cell counts and absolute white blood cell counts. Differential counts are defined as the proportion of the total white blood cells that each white blood cell type makes up. The five types of white blood cells considered in the present case are monocytes, lymphocytes, eosinophils, basophils and neutrophils. The absolute count for a given cell type is the total number of cells of that type per unit volume of blood.

The four main processes can be summarised as follows:
(1) Frame by frame object classification to obtain classification results for objects in each frame of the flowing blood sample.
(2) Differential counts by tracking objects from one frame to the next over multiple frames to obtain an overall object classification for each tracked object in order to obtain the differential counts.
(3) Absolute count for all white blood cell types by obtaining the absolute white blood cell count from all of the objects whose classification results indicates that they belong to one of the five white blood cell types using speed-adaptive sampling or statistical analysis of the captured frames.
(4) Absolute count for each white blood cell type by using results from processes (2) and (3) to obtain the absolute white blood cell count for each of the five white blood cell types.

The structure and operation of an embodiment of a device for carrying out processes (1) to (4) will now be described.

Structure and Operation of Device

Figure 1A:
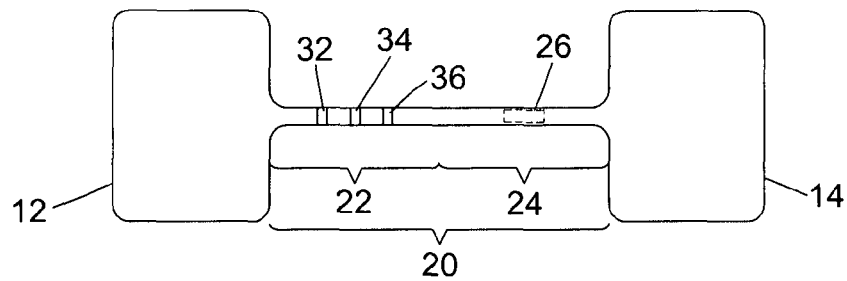
FIGS. 1a-c illustrate views of a microfluidic liquid handling structure.
Figure 1B:
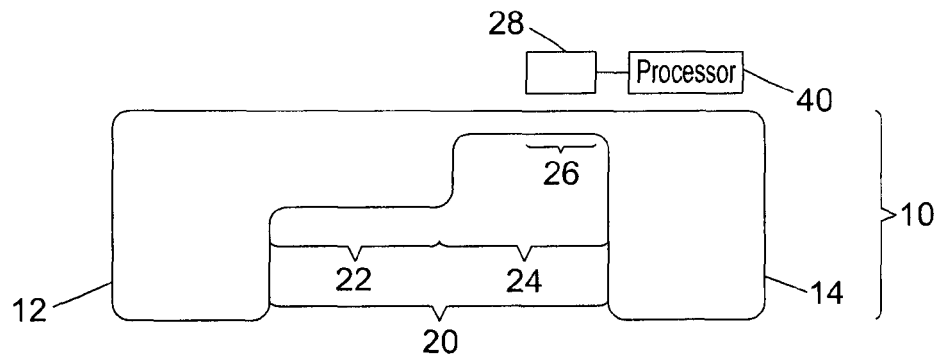
Figure 1C:
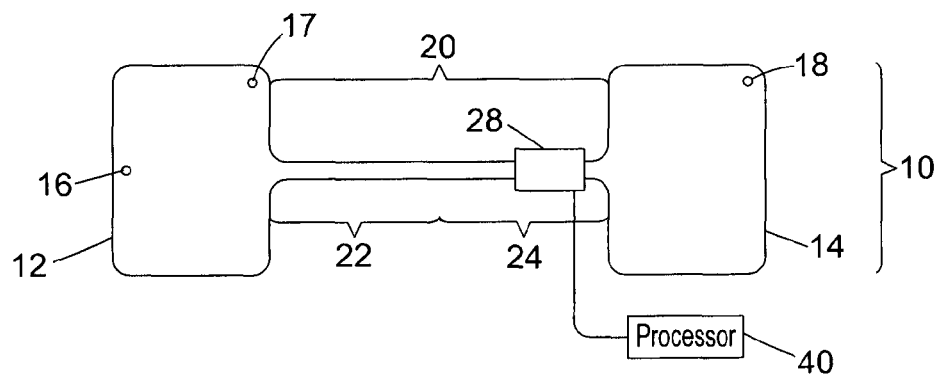

Referring to FIGS. 1A and 1B, a device 2, for the classification and counting of white blood cells within a blood sample is described. The device 2 includes a microfluidic liquid handling structure 10. FIGS. 1A and 1B illustrate mutually perpendicular cross-sections of the device 2, including the microfluidic liquid handling structure 10. FIG. 1C illustrates the device 2 as viewed from above.

With reference to FIG. 1C, the microfluidic liquid handling structure 10 comprises the following main elements: a loading chamber 12, a connection conduit 20 and a waste chamber 14. The loading chamber 12 has a sample inlet 16 through which a blood sample can be introduced into the microfluidic liquid handling structure 10. The inlet 16 is sealable in order to, when sealed, prevent the sample escaping once it is in the microfluidic liquid handling structure 10. The waste chamber 14 and the loading chamber 12 have air vents 17, 18 such that the chambers are open to the atmosphere. This allows the blood sample to flow from the loading chamber 12, through the conduit 20 and into the waste chamber 14 by capillary action. The microfluidic liquid handling structure forms part of a cartridge insertable into a holding structure for holding the cartridge relative to an image capture device 28. In some embodiments, the cartridge may come with a custom metering implement for metering an appropriate volume of blood for application to the microfluidic liquid handling structure, for example a pipette.

In some embodiments, the microfluidic liquid handling structure 10 is sealed from the atmosphere when the inlet 16 is sealed and the microfluidic liquid handling structure includes a network of air channels including an air circuit which connects the loading chamber 12 and the waste chamber 14. The air circuit allows air to escape from the waste chamber 14 into the loading chamber 12 as the blood sample flows from the loading chamber 12 and fills the waste chamber 14. The air circuit includes one or more flow barrier valves, for example a sudden expansion of the air circuit, to prevent the sample from entering the air circuit by capillarity.

Sharp angles within the microfluidic liquid handling structure 10 are preferably avoided to reduce impediments to sample flow and to prevent trapping of air bubbles inside the connection conduit 20 whilst the waste chamber 14 is filing with the blood sample. The connection conduit 20 comprises two portions: a preparation portion 22 and a detection portion 24. The preparation portion 22 is arranged for the lysing of red blood cells and staining of white blood cells. As the sample moves through the preparation portion 22, it encounters a series of patches of dry reagents 32, 34, 36. Although in FIG. 1A three patches of dry reagents are provided, it will be appreciated that any number (one or more) patches may be provided within the preparation portion 22. As the blood sample flows over the one or more patches, it will dissolve the reagent(s) which will gradually diffuse through the blood volume and prompt a chemical reaction. The dynamics of such reactions depends mainly on the blood flow rate and the length(s) of the patch(es) of dry reagent. The content of dry reagent stored in the preparation portion 22 and how easily it dissolves in blood will also have an effect on the dynamics. The dry reagents comprise, for example, a haemolytic agent for the selective lysing of red blood cells and the staining agent is for differential staining of white blood cells and a staining agent. A staining agent from the family of hematoxylin and eosin (H&E) stains, Romanowsky stains, methacromatic stains or any combination thereof can be used. From combinations of colour information with morphological features like granularity, size, shape of the cell cytoplasm and nucleus, it is then possible to obtain a set of distinct signatures for each of the sub-populations under study. Further discussion of the use of reagents can be found in application WO2013135713, which is incorporated herein by reference.

In one specific embodiment, the preparation portion 22 contains a series of 2 sequential reagents, comprising a first reaction site which is 10 mm long comprising a mixture of surfactant and lytic agent (Surfynol and saponine, respectively) and a 10 mm long reaction site with a mixture of stains. In this embodiment, the mixture of stains includes a mixture of eosin, methylene blue and basic orange 21 leading to differential colours for a 5-part classification of white blood cells: lymphocytes stain blue, monocytes stain blue/purple, neutrophils exhibit blue nucleus and pale yellow cytoplasm, eosinophils exhibit blue nucleus and dark yellow granules, basophils stain bright pink.

The detection portion 24 of the connection conduit 20 is where the cells are, in operation, imaged and counted. The detection portion 24 is aligned with a field of view 26 of an image capture device 28, such that the blood flowing through the detection portion 24 flows across the field of view 26 of the image capture device 28. Approximately two thirds of the width of the detection portion 24 is within the field of view 26 of the image capture device 28. The image capture device 28 is positioned above the detection portion 24. The image capture device 28 includes a lens arrangement and a focusing mechanism for focusing on the blood sample flowing into the detection portion 24 to image the lysed and stained sample when it is in the detection portion 24.

The detection portion 24 is arranged to be shallower than preparation portion 22, such that it accommodates a single layer of objects which move across the field of view 26 of the image capture device 28. It is preferable to ensure that a single layer of objects move across the field of view of the image capture device 28 to increase the chance that each object is counted and to facilitate the classification of the objects. If multiple layers of objects were provided in the field of view then some objects could be blocked from view completely and others could be partially obscured by other objects. Having a single layer of objects also facilitates any defining characteristics of objects (including cells) being captured. The preparation portion 22 is deeper than the detection portion 24 to facilitate the arrangement of the reagents 32, 34, 36 and to increase their surface areas. The reduction in depth from the preparation portion 22 to the detection portion 24 facilitates sample flow by capillarity through the detection portion 24. Further, the depth of the preparation portion is increased to facilitate homogeneity of lysis and staining of the blood cells.

Figure 2:
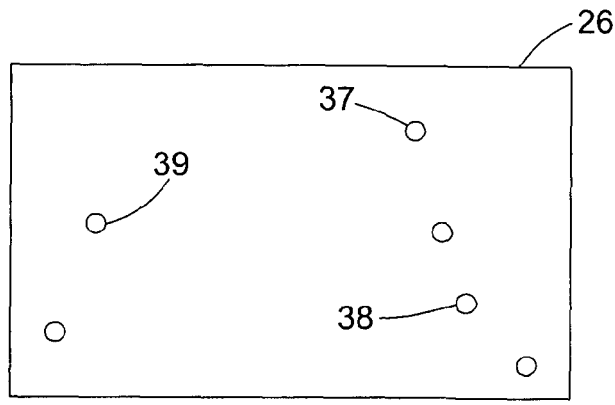
FIG. 2 illustrates a schematic view of white blood cells in the detection portion.

In some embodiments, the detection portion 24 is at least twice as wide as the estimated largest dimension of any object to be detected and its depth is less than twice this largest dimension. In one embodiment, the detection portion 24 is 15 mm long, 0.06 mm wide and 0.02 mm deep. This configuration defines a volume for the detection portion 24 of 0.018 pt. FIG. 2 schematically illustrates the type of image obtained with several stained white blood cells 37, 38, 39 in such a detection portion.

Associated with the device 2 is a processor 40 configured to carry out the data processing required to obtain the cell counts. The processing steps will be described below.

The operation of the device 2 will now be described. The sample is introduced into the microfluidic liquid handling structure 10 through the inlet 16 and the inlet is then sealed. The sample enters the loading chamber 12 and is drawn by capillary action into the preparation portion 22, and, subsequently, into the detection portion 24. Therefore, once the blood sample enters the detection portion 24, it has already reacted with the red blood cell lytic agent and differential stains for white blood cells.

The image capture device 28 may initially be out of focus, but when the sample enters the detection portion 24 and subsequently the field of view of the image capture device 28, a focusing mechanism focuses the image capture device 28 on the sample and the image capture device 28 begins capturing images as frames of a video. Focusing methods, implemented in software and/or hardware are generally well known. A specific example adapted for use with the device 2 is disclosed in UK application number 1417170.6 incorporated herein by reference. In one specific implementation, the video is taken for four minutes at a rate of 15 frames per second, resulting in approximately 15-30 frames being captured of each cell. Frame acquisition durations and rates are adapted to the specific flow in the microfluidic liquid handling structure 10 to capture a sufficient number of frames per cell for subsequent analysis. Durations and times are readily adapted by a skilled person to optimise data collection according to the circumstances. During the assay, approximately 1500 cells move across the field of view 26 of the image capture device 28 in one example, for a healthy sample. The data obtained from the video consists of a series of frames (approximately 4000), wherein each frame comprises an image containing one or more cells and other objects, such as clusters of cells or platelets. Some frames may contain no objects at all and these frames are discarded.

In order to count cells in the sample, the cells (and any other objects moving across the field of view of the image capture device 28) must be classified. Since the image capture device 28 is capturing frames as cells move across its field of view, a number of images of the cell in different positions within the field of view 26 will be obtained. As the cells move across the field of view 26 they are typically also rotating. If a cell is non-isotropic, i.e. does not look the same from all directions, the frames taken of the cell as it rotates will differ. A number of cell types are known to be non-isotropic and the fact that the frames taken will differ is exploited in the present invention in order to classify and count cells and other objects, as described below. Frames will also differ due to the imperfect optics used to image the sample.

Having described a device used for the various processes briefly introduced above, such processes are now described in detail.

Object Classification

A method used to classify the objects in a frame is now described with reference to FIG. 3. Each frame is first segmented into object and background pixels at step 42, using thresholding in some embodiments, for example Otsu's method, and the objects in the frame are identified at step 44, as is well known in the art of image processing. At step 46, each object is given an identifier which is unique to that object and frame and at step 48, a list of the object identifiers and their associated object positions is obtained. Image patches centred on the object positions are extracted at step 50. Then, for a first image patch, the image patch is segmented into separate object regions at step 52. These regions are, in overview: background; nucleus of the cell; cytoplasm.

In some embodiments, a k-means clustering algorithm based on RGB colour values is used for segmentation. The pixels of each image patch are clustered using k-means (or any other suitable clustering algorithm) on the RGB values of the pixels to define three clusters. This results in a mask with a cluster identifier (cluster 1, cluster 2, cluster 3) for each pixel. The cluster with the darkest (e.g. average) pixel intensity or colour is labelled as the nucleus, the cluster with the lightest (e.g. average) pixel intensity or colour is labelled as background and the remaining cluster is labelled as cytoplasm. The segmentation algorithm therefore outputs three regions, which are identified as background, nucleus and cytoplasm according to the intensity or colour of each region.

In some embodiments, as a refinement, k-means clustering used again to split pixels previously identified as the nucleus, to cluster these pixels into two sub-regions: nucleus and 'cytoplasm region 2'. This may help to more accurately define the boundary between the nucleus and cytoplasm. In this step, pixels labelled as nucleus are either left as 'nucleus', or are reclassified as 'cytoplasm region 2'.

In some embodiments, an alternative segmentation approach can be applied, which advantageously may be more robust against image variations. The approach involves the following steps for each image patch:

1) k-means clustering with k=2 to separate cell (darker pixels) from background (lighter pixels);
2) label background pixels as background and mask (set to a predefined colour, say green);
3) k-means clustering with k=3 to get nucleus (darkest), cytoplasm (lighter) and the now, say, green background;

4) label cytoplasm pixels as cytoplasm region 1 and mask cytoplasm in addition to the background by setting cytoplasm pixels to the predefined colour;

5) k-means clustering with k=3 to get nucleus pixels (darkest), cytoplasm region 2 and the now masked background (which now includes the previous cytoplasm region 1 area);

6) label nucleus pixels as nucleus and cytoplasm region 2 pixels as cytoplasm region 2.

In embodiments in which only one cytoplasm region is segmented, the clustering stops after step 3 with labelling the nucleus and cytoplasm pixels accordingly.

In some embodiments, the 'cytoplasm region 2' region is merged with the cytoplasm identified in the first pass ('cytoplasm region 1') and labelled as an overall cytoplasm for the further analysis/cell classification. In other embodiments, 'cytoplasm region 1' is taken as representative of the cytoplasm. Noting that 'cytoplasm region 2' is a transition region between the nucleus and cytoplasm of the cell, object parameters for this region are used in classifying objects in addition to the overall cytoplasm, in some embodiments.

Overall, each object is split into three or four regions, depending on the embodiment: nucleus; background; cytoplasm; cytoplasm region 2, or: nucleus; background; cytoplasm.

Examples of other clustering based algorithms for identifying blood cells can be found in 'White Blood Cell Segmentation by Color-Space-Based K-Means Clustering', Congcong Zhang et al, Sensors 2014, 14, 16128-16147; doi:10.3390/s140916128; 'Leukocyte segmentation and classification in blood-smear images', Herbert Ramoser et al, Proceedings of the 2005 IEEE Engineering in Medicine and Biology 27th Annual Conference, Shanghai, China, Sep. 1-4, 2005, all incorporated herein by reference, and may be used for object segmentation in some embodiments. It will be understood that any other suitable segmentation method, supervised or unsupervised, using clustering or other techniques, may be used in some embodiments. Specifically, any suitable alternative clustering algorithm other than k-means may be used in any of the above embodiments.

For objects which are not cells and hence do not have a nucleus or cytoplasm, the k-means algorithm still splits the object up into multiple regions but these regions are not meaningful and the convergence of the k-means algorithm is not as good for non-cell object as that for cells. Non-cell objects are identified by the classifier discussed below.

At step 54, object parameters are extracted for the identified cell regions from each image patch for each of the respective objects. These parameters include:

image saturation averaged over the relevant pixels and its standard deviation intensity averaged over the relevant pixels and its standard deviation, colour averaged over the relevant pixels and its standard deviation, object roundness, $$\text{compactness} = 2\frac{\sqrt{\pi * \text{object area}}}{\text{object perimeter}},$$

for example $$\text{form factor} = \frac{4\pi * \text{object area}}{(\text{object perimeter})^2},$$

for example
  object perimeter,
  object area and
  focus quality of the image.

FIG. 4 shows a list of object parameters that may be extracted for each of the respective objects in an embodiment in which objects are split into four regions.

The values of some parameters are extracted for the object as a whole, for example the object roundness and the object perimeter. The values of other parameters are extracted for each object region, for example the intensity and colour and their standard deviations, using masks to isolate each region in turn. The values for the background region are used for calibration. For example, they are used to account for more staining in one region of the field of view 26 than another. If the focus quality of an image is too poor, for example if it is below a predetermined threshold, then that image is discarded.

At step 56, the values of the extracted parameters are then used with a Logistic Model Tree classifier to obtain classification results, a discussion of which may be found in N. Landwehr, M. Hall and E. Frank, 'Logistic Model Trees', Machine Learning, vol. 59, pages 161-205, 2005, incorporated herein by reference. The classifier is trained prior to its use for classification using expert labelled training data. The Logistic Model Tree classifier is used to obtain class-belonging scores for each object, e.g. probabilities of each object belonging to each object type. In some embodiments, the SimpleLogistic class provided by the Weka collection of machine learning algorithms is used (see Class SimpleLogistic by Authors Niels Landwehr and Mark Sumer; Weka 3: Machine Learning Software in Java, both incorporated by reference herein and available online). Any suitable classifier, for example a Support Vector Machine can be used, as will be apparent to a person skilled in the art. Steps 52-56 are repeated for each object in the frame.

The object types include five white blood cell types, nine other object types, used for objects other than white blood cells to be counted, and a 'cell cluster' classification. The object types are:
  lymphocyte
  monocyte
  neutrophil
  basophil
  eosinophil
  'unstained cell'
  'cluster of cells'
  'background object'
  'large debris' (e.g. aggregate of platelets, undissolved stain)
  'out-of-focus cell'
  'red blood cell'
  'nucleated red blood cell'
  'out of range'
  'other'
  'eosinophil within a cluster'

The above object types or classes are largely self-explanatory. 'Out of range' refers to objects that do not lie entirely within the frame and hence only part of the object can be seen. 'Other' refers to any debris that does not fall into one of the other classifications.

If a blood sample contains too many objects in any one of the non-white blood cell (i.e. other than the first five) classifications (for example if the proportion of objects classified as an 'other' type exceeds a threshold) then the results of the assay may be discarded.

The 'eosinophil within a cluster' classification is useful because eosinophils make up a very small proportion of all white blood cells. If those eosinophils contained in a cluster of cells were ignored and not counted, then very few or even no eosinophils would be counted in a given assay.

Typically, a cluster of cells is characterised by a large object area, for example 500 pixels or more. Therefore, object area is discriminative of clusters of cells. An eosinophil has a distinct colour signature and as such, the mean (or median or other overall measure) of colour of the cluster as a whole is shifted. By identifying this shift in colour, the presence of an eosinophil within the cluster is detected. As detecting an eosinophil within the cluster is a relatively rare event, in contrast to detecting other objects, it is assumed that if the shift in colour of the cluster is detected, that the cluster contains one eosinophil, in some embodiments. Further processing to count eosinophils in identified clusters is used in other embodiments. Any of the above method steps may be carried out by or under the control of a processor.

Including a cell within a cluster in estimating a cell count can be implemented alone or in combination with other disclosed features and steps. This technique may also be applied to other cell types, for example Basophils.

Figure 3:
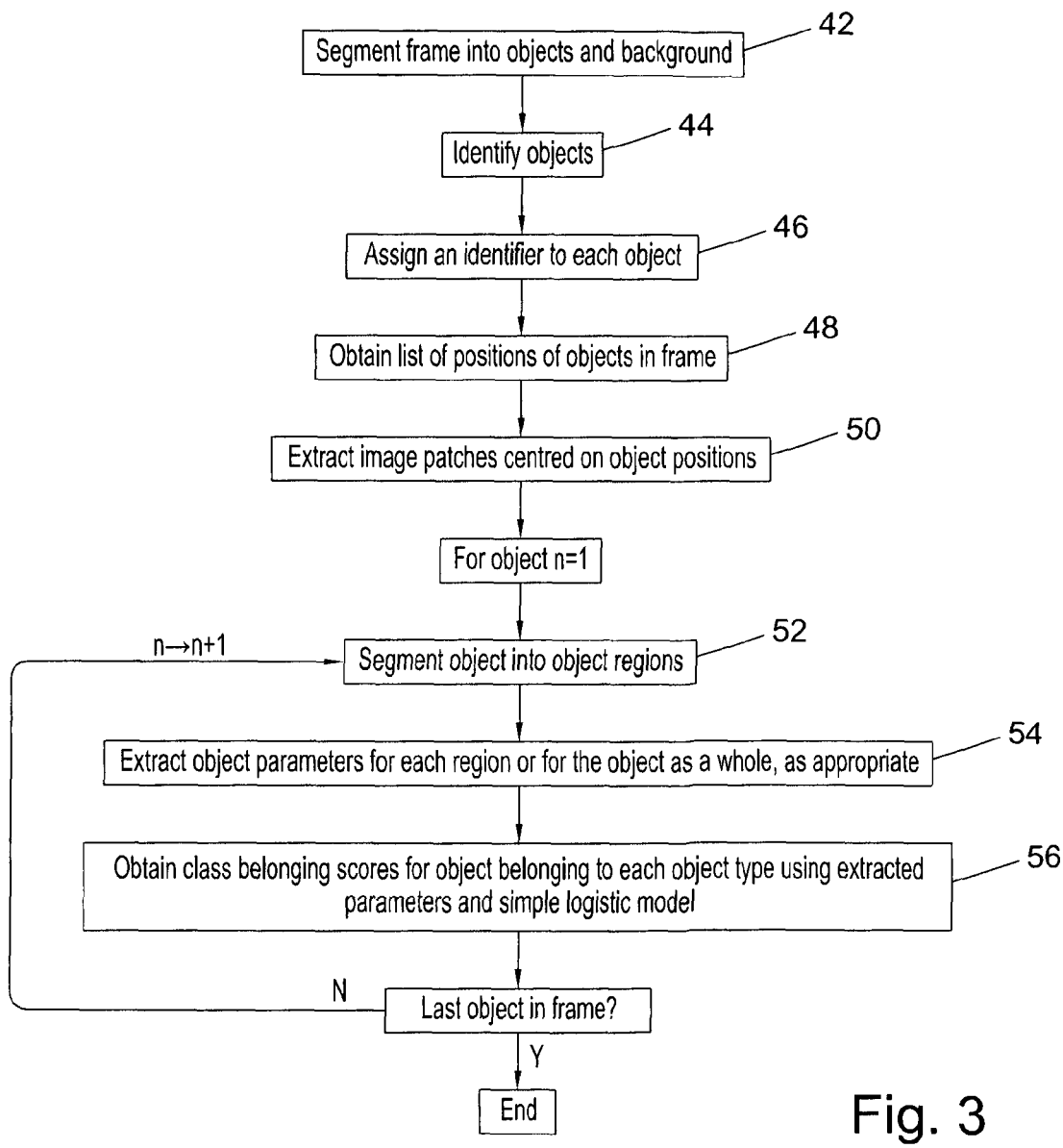
FIG. 3 illustrates a flow diagram representing a method for obtaining classification results for objects within a frame.
Figures 5, 6:
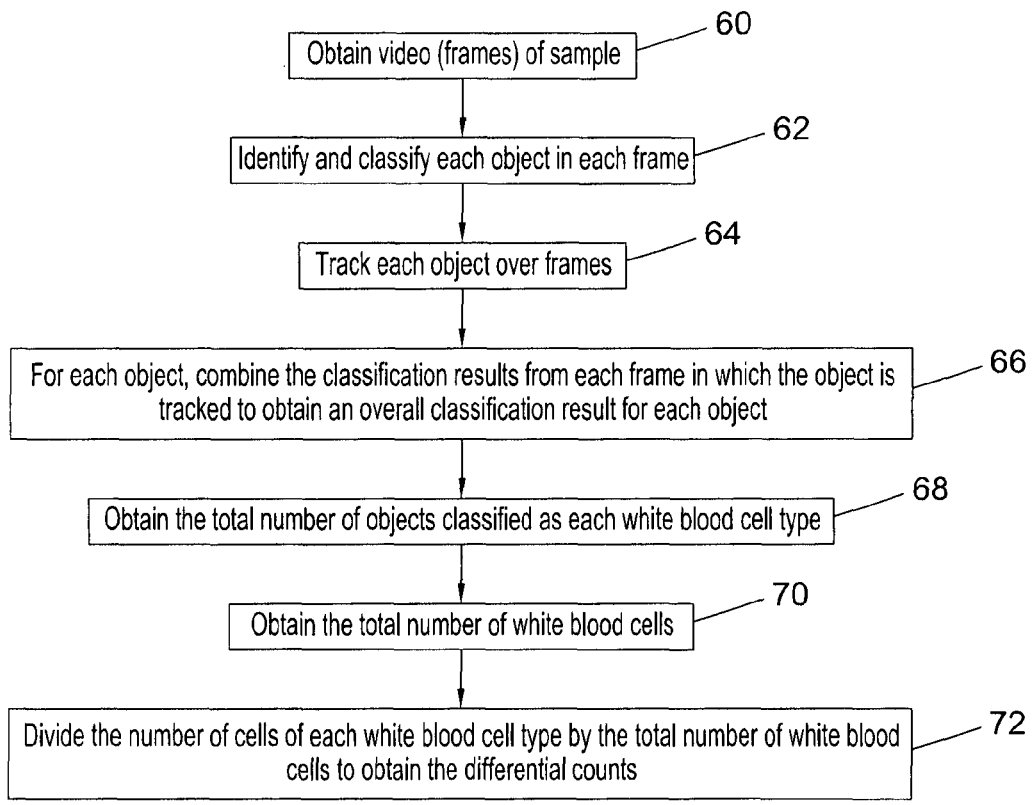
FIG. 5 illustrates an example of class-belonging scores for each object type for each frame for a given object.
FIG. 6 illustrates an overall method for estimating the differential cell counts

The process described with reference to FIG. 3 is repeated for as many frames as necessary. An example of the data obtained for a given object is illustrated in FIG. 5.

Differential Counts

A method of obtaining differential counts is now described with reference to FIG. 6. At step 60, a video comprising a number of frames is taken of the blood sample, according to the methods described above. At step 62, the objects in each frame are identified and class belonging scores are obtained using the simple logistic model. This process is described above with reference to FIG. 3. At step 64, each object is tracked across as many frames as possible, as is now described with reference to FIG. 6. As the sample flows across the field of view 26, each object in the sample typically remains in the field of view 26 of the image capture device 28 for 1-2 seconds. Therefore, a given object will appear in approximately 15-30 frames. The object is then tracked from one frame to the next. This tracking process will now be described with reference to FIGS. 7 & 8.

Figure 7:
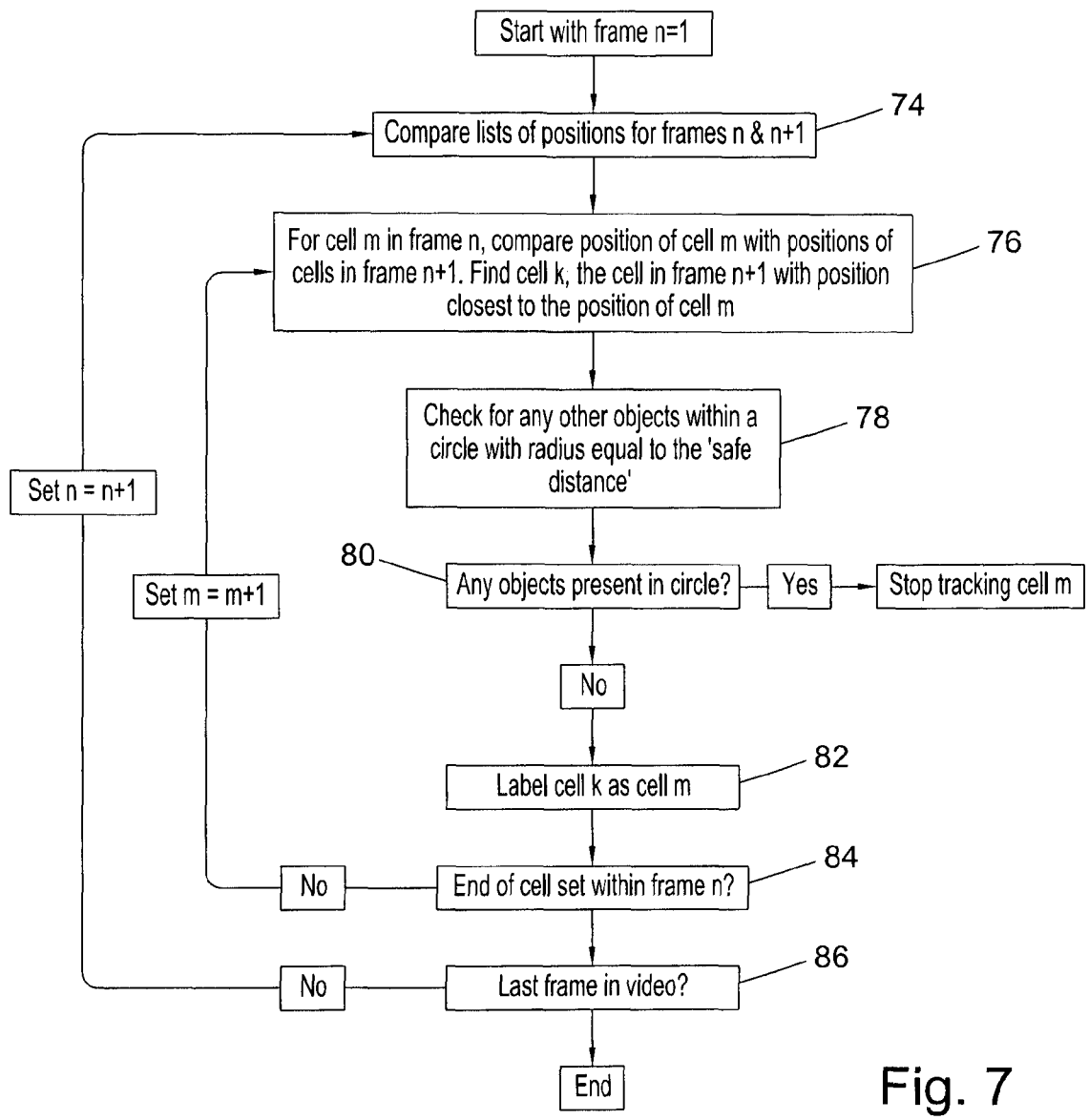
FIG. 7 illustrates a method for tracking objects across multiple frames.
Figure 8:
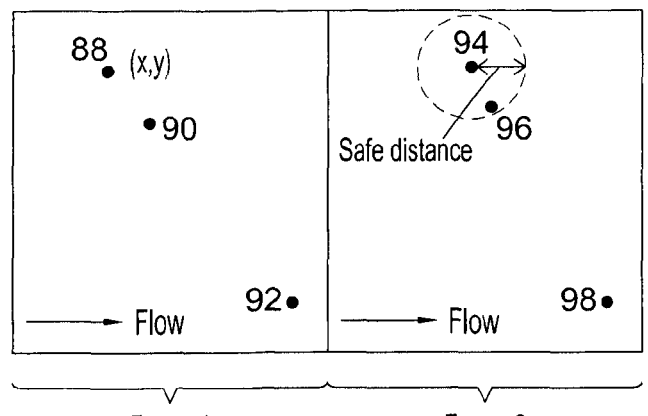
FIG. 8 illustrates two consecutive frames of the blood sample.

With reference to FIG. 7, having obtained a list of object positions during the frame by frame classification of the objects, as described above, the list of object positions for frame 1 is compared to the list of object positions for frame 2 at step 74. For a first object 88 (see FIG. 8) at position (x, y) in the first frame, an object 94 in a second frame which has the position closest to position (x, y) is identified. At step 78, a check is carried out to determine whether any other objects lie within a circle centred on object 94, with radius equal to a predefined 'safe distance'. This 'safe distance' is defined as a distance at which two objects are too close to be distinguishable with confidence from each other from one frame to the next. At step 80, if an object 96 is within the safe distance from object 94 then object 88 cannot be identified in the second frame and the tracking of object 88 stops. If at step 80, no objects within the safe distance from object 94 are found, object 94 is identified as being the same object as object 88 in the previous frame. Steps 76-84 are repeated for all objects in the first frame such that each object is either tracked from frame 1 to frame 2, or cannot be identified with enough certainty in frame 2. In the latter case (conflicting object within safe distance), the tracking of these objects stops. The process then moves onto the next frame, at step 86, and the lists of positions for frames 2 & 3 are compared. Steps 74-86 are repeated for all frames in the data set until lastly, the lists of object positions for frames n-1 and n are compared, where the data set consists of n frames.

In some embodiments, object velocity is used to improve tracking. Rather than picking the object 94 in frame 2 that is closest to object 88 in frame 1 at step 76, the object closest to the predicted position of object 88, based on the velocity of object 88 determined from frame 1 and one or more previous frames, is picked, which enables a reduction of the safe distance, since more information is used in the tracking. This is carried out, in some embodiments, in the tracking of an object from a second to a third frame and for subsequent frames thereafter, but not from a first to a second frame, because the velocity of the object is estimated by analysing more than one frame.

It will be appreciated that any given object will appear in 15-30 frames but not all of the frames may be used to classify the object if tracking of the object stops before it leaves the field of view 26 of the image capture device 28 or a 'collision' is detected at step 80.

In tracking the objects, a set of image patches for each tracked object is obtained. In other words, the objects (image patches) obtained in the method described above with reference to FIG. 3 are 'matched up' with other objects (image patches) which correspond to the same object.

Returning to FIG. 6, having obtained the class-belonging scores for each tracked object for each individual frame (steps 62 and 64), an overall classification for each cell is determined at step 66. This may be done in a number of ways, which will be described below.

In some embodiments, the class-belonging scores are averaged across all frames for a given object. The class with the highest score is taken to be the class to which that object belongs. i.e. for the first type, 'lymphocyte' for example, the scores for the object for the object type 'lymphocyte' are averaged across all frames. The same is done for 'monocyte', 'eosinophil' . . . and so on for all object types. The object is then determined to belong to the type which has the highest averaged score.

Figure 9:
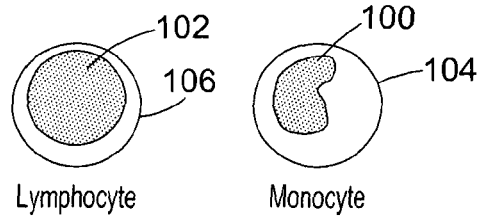
FIG. 9 shows a schematic diagram of a monocyte and a lymphocyte.

In other embodiments, the averaging described above is carried out, but a rule is set such that the result of the averaging can be 'overridden' by one or more pre-set events. With reference to FIG. 9, a monocyte typically has a 'bean-shaped' nucleus 100, whereas the nucleus 102 of a lymphocyte is rounder. However, a monocyte 104 viewed from certain angles (where the 'bean' shape of the nucleus cannot be identified, for example) can be similar in appearance to a lymphocyte 106. For example, since a monocyte moving across the field of view of the image capture device 28 is also rotating, in most of the frames, it might be captured at an angle in which the 'bean' shape of its nucleus cannot be seen. As it rotates, the 'bean' shape of the nucleus may be visible in one or two frames but then as it continues to rotate, it may come to look like a lymphocyte again. Therefore, 10 out of 12 frames may indicate that the object is a lymphocyte but only two indicate that it is a monocyte, when the object is in fact a monocyte. If the averaging method described above were employed, then the cell may be incorrectly classified as a lymphocyte overall. However if a rule is set such that this classification can be overridden if, for example, at least one frame indicates that the object is a monocyte, then the cell would be correctly classified as a monocyte. For this reason, in some embodiments, if the class-belonging score for the cell being of the object type 'monocyte' for at least one frame (or at least two or at least another predetermined number of frames) is above a threshold, 90% for example, the cell is determined to be a monocyte, regardless of the values of the scores for the other frames and cell types.

In other embodiments, a 'voting' process may be employed. In this embodiment, each frame is given a vote, wherein the vote for each frame corresponds to the object type with the highest class-belonging score for that frame. The object is then determined to belong to the object type with the most votes.

In further embodiments, the 'voting' system of the previous embodiment may be employed, but a certain object type has an overriding vote. If at least one frame or more than a pre-set number of frames votes 'monocyte', for example, then the object is classified as a monocyte overall, regardless of the votes from the other frames.

In a further embodiment, no averaging is carried out and the overall classification for a cell may be determined based only on such rules as described above.

Figure 10:
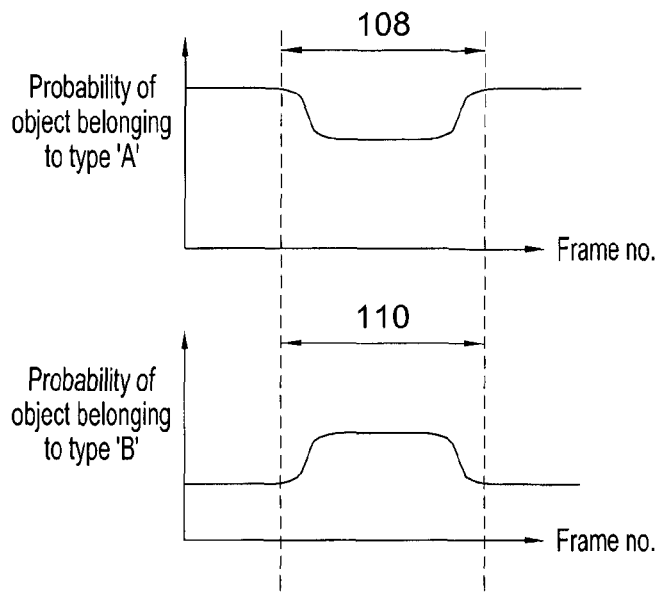
FIG. 10 shows a graphical representation of the class-belonging scores for an object for two different object types 'A' and 'B' across multiple frames.

With reference to FIG. 10, a moving average is calculated in some embodiments in order to determine the overall classification. A window of three frames, for example, is placed at that start of the set of frames and the class-belonging scores are averaged across these three frames. The window is then shifted along by one frame and the next average is calculated. This process is repeated until all of the frames in the set have been covered. Calculating such a moving average can be advantageous because the object is likely to be rotating relatively slowly compared to its movement across the field of view of the image capture device 28. In other words, an object is unlikely to be in one orientation in one frame and then suddenly switch to an entirely different orientation in the next frame. With reference to FIG. 9, the class-belonging score for a certain object for a type 'A' drops in region 108 and simultaneously, the class-belonging score for a type 'B' rises in region 110. This type of signature may occur as an object rotates as it moves across the field of view 26 of the image capture device 28 and a distinguishing characteristic of an object type, such as the 'bean' shape of the nucleus of a monocyte, becomes detectable. Therefore, in some embodiments, characteristic patterns as the one described above may be used to derive an overall classification.

In yet another embodiment, a weighted average may be used to determine the overall object classification. Each frame is given a weight which depends on the optical quality of the frame and the position of the frame within the set of frames. In one embodiment, the weight given to a frame increases with the optical quality of that frame and varies inversely with its distance from the central frame within the frame set. Accordingly, the first and last frames in the set are given less weight than the intervening frames.

If the results of any of the above methods for determining an overall classification for an object are inconclusive, then that object may be classified as 'unknown'. This may occur, for example, when half of the frames for a given object indicate that the object belongs to one object type and the other half indicate that the object belongs to another object type. In this case, it may not be possible to determine with any sort of certainty which class the object belongs to and so the object is classified as 'unknown'. An assay in which many objects are classified as 'unknown' may be discarded and the results considered unreliable. This may be done when the proportion of objects classified as 'unknown' exceeds a pre-set threshold, for example.

The differential cell counts are calculated based on the total number of cells classified as each cell type. To obtain the differential white blood cell counts, the total number of white blood cells is first calculated by summing the number of cells in each of the five white blood cell classes: lymphocytes, monocytes, eosinophils, neutrophils and basophils. The proportion of white blood cells that each class makes up is then found by dividing the number of cells of a given cell type by the total number of white blood cells detected. Typical values for differential white blood cell counts are shown in the table below.

| Cell type | Proportion |
| --- | --- |
| Neutrophils | 0.6 |
| Lymphocytes | 0.3 |
| Monocytes | 0.06 |
| Eosinophils | 0.035 |
| Basophils | 0.005 |

Once the proportion of cells that each cell type makes up is known, the absolute counts for each cell type can then be determined if the total volume of the sample is known. However, the total volume of the sample may not be accurately known. The volume of the sample could be determined based on knowledge of the blood flow rate through the connection conduit 20, the dimensions of the connection conduit 20 and the time of flow during frame acquisition, however flow rates are variable and factors such as air bubbles in the microfluidic liquid handling structure make it difficult to accurately determine the volume of the sample. To accommodate a potential lack of total volume information, different methods can be employed in some embodiments to obtain the absolute cell counts. Some of these methods are described below, turning first to methods for obtaining an absolute count for all white blood cells (of all types).

Absolute Counts

Absolute Count Method 1—Statistical Analysis

As mentioned above, another useful quantity to determine is the absolute white blood cell count. This is the estimated number of white blood cells per unit volume of blood. Although the total volume of the blood sample used in the assay is not accurately known, the volume of blood which is within the field of view of the image capture device 28 at any one time is the product of the area of the field of view and the depth of the detection portion 24. This fact is used in estimating the absolute count.

The above means that the depth of the detection portion is such that all objects flowing through the detection portion can be imaged by the image capture device. This will be the case where the depth is of the order of white blood cell sizes, for example less than twice the largest cell dimension. If the detection portion is deeper than that, the depth of the detection portion is, in some embodiments, replaced by the depth of focus of the image capture device, throughout which all objects flowing through the corresponding cross-section can be imaged, for the purpose of calculating the volume of blood which is within the field of view of the image capture device 28 at any one time.

In an embodiment, the absolute white blood cell count is estimated using a statistical analysis. This process of estimating the absolute white blood cell count is described with reference to FIG. 11.

At step 112, the first four hundred frames in the set of frames obtained in taking the video of the blood sample are discarded. This is because these first four hundred frames typically contain a significant amount of debris, such as platelets.

At step 114, the white blood cells in each frame are identified and counted in each frame. Having already obtained class-belonging scores for the objects according to the method above, an object is counted as a white blood cell if it has a highest class belonging score for one of the five types of white blood cell. Alternatively, objects classified for counting purposes as white blood cells by summing all white blood cell class belonging scores and making the classification if the sum is greater than the sum of scores for the objects being of a non-leukocyte type (or a fixed threshold, for example 0.5 if the scores are probabilities).

At step 116, the remaining set of frames is split up into blocks, where each block contains approximately 1200 frames. Block 1 contains the first one thousand two hundred frames, block 2 contains the second one thousand two hundred frames and so on. At step 118, for each block, a Gamma distribution with parameters $\alpha$ and $\beta$ is fitted to the distribution (histogram) of white blood cell counts from each frame in that block. A goodness of fit measure for each fit is obtained. The mean cell count per frame within each block, $\mu$, is then found at step 120 as:

$$\mu = \alpha\beta \qquad (1)$$

where $\alpha$, $\beta$ are the parameters of the Gamma distribution fitted to the count data of the respective block.

In another embodiment, a Poisson distribution with parameter $\lambda$ (corresponding to the count per frame expected under the distribution) is fitted to the distribution (histogram) of white blood cell counts across the frames in each block and as before, a goodness of fit measure is obtained. The mean cell count per frame within each block is taken to be the parameter $\lambda$ of the Poisson distribution.

At step 122, the value of the mean determined for one of the blocks is selected to be used to determine the overall estimate of the absolute white blood cell count. The value of the mean itself and the corresponding goodness of fit of the distribution is taken into account when choosing which value to use. As a starting point, the value of the mean for the first block of frames is considered. If a subsequent block has a better goodness of fit measure and the value of the mean for that block is not significantly lower than that of the first block (it is within 10% of the value for the first block, for example), then the value of the mean from that subsequent block is used to determine the overall estimate of the absolute white blood cell count. For example, if the value for the second block is similar to the value corresponding to the first block, for example it is only slightly lower, but the second value has a better goodness of fit measure, then the value for the second block is used. A value of a mean may be determined to be 'similar' to another value if it is within 10% of it, for example. If no such subsequent block with a better goodness of fit measure and a similar mean exists, the value of the mean from the first block is used. In obtaining an estimate of the mean cell count from a distribution fit to a block of frames in this way, it is advantageous to fit the distribution to frames over which the rate of flow of the blood sample is substantially constant. A substantially constant flow rate means that every object is likely to appear in approximately the same number of frames. Conversely, a variable flow rate would result in slow-moving cells appearing in many frames and faster-moving cells appearing in relatively few frames. To increase the likelihood of the flow being substantially constant over the frames to which a distribution is fitted, frames with an average object speed below a threshold are discarded, in some embodiments. For example, objects are tracked across frames, as described above, and the average object speed in each frame evaluated.

Any frames for which the average object speed is below a predetermined threshold are then discarded and not considered in estimating the mean number of white blood cells per frame.

In some embodiments, additionally or alternatively, the dimensions and configuration of the microfluidic structure can be designed such that the rate of flow of blood sample through the detection portion can be considered substantially constant after a certain period of time has elapsed since the blood sample first reaches the detection portion, for example three seconds. A block of frames could then be selected, for the purpose of estimating the mean cell count per frame, which only includes frames after this time period has elapsed. In yet further embodiments, flow may be monitored otherwise and frames with too slow a flow, or blocks of flames with flow variability of flow speed above a threshold, discarded.

Having obtained an estimate of the mean cell count per frame, an estimate of the overall absolute white blood cell count is then obtained. The absolute count is based on both the mean (estimated) count and a blood volume associated with the count. The volume of blood 'captured' in a single frame, i.e. the volume of blood that is contained within the field of view of the image capture device 28, referred to as $V_{FOV}$, can be calculated using equation (2):

$$V_{FOV} = d*w*h \qquad (2)$$

where d=depth of the detection portion 24, w=width of the field of view of the image capture device 28 along the direction of blood flow, and h=height of the field of view, i.e. the depth of the detection portion in the extent of the field of view across the detection portion 24, as discussed above.

Figure 12:
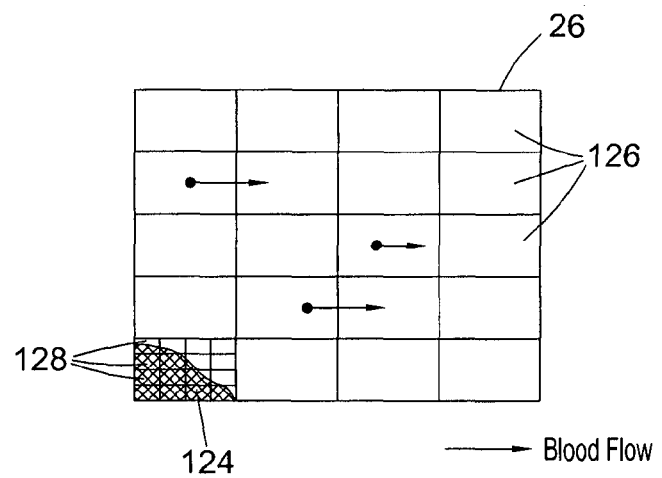
FIG. 12 shows a schematic diagram of the field of view of the image capture device split up into regions for the purpose of correcting for an obstruction.

In some embodiments, the value of $V_{FOV}$ is calculated online based on the dimensions of the detection portion, as described above. In other embodiments, information relating to $V_{FOV}$ may be part of a set of calibration data that comes with the microfluidic liquid handling structure 10, for example on a cartridge on which the microfluidic liquid handling structure is provided, or with a tag readable by the device 2 attached to the cartridge or packaging containing the microfluidic liquid handling structure 10. In some embodiments, the accuracy of the determination of $V_{FOV}$ is verified by carrying out a check for any obstructions in the field of view. With reference to FIG. 12, examples of such obstructions could be an aggregate of platelets or cells or an air bubble. Such an obstruction 124 with volume $V_{OBS}$, in the field of view 26 would mean that the volume associated with the field of view is not entirely filled with blood. This would lead to an overestimation of the volume of the blood sample and hence an underestimation of the absolute white blood cell count.

To overcome this problem, a check is carried out for any such obstructions. This is done by splitting the field of view up into regions 126. The average number of objects passing through each region in a given time is recorded. If the average number of objects for any region is less than a certain threshold, then it is determined that there is an obstruction in that region. That region is then split up into further sub-regions 128, each comprising a small number of pixels. The pixels within the obstructed volume will have no objects passing across them and so by identifying these pixels with zero passing objects, the area of the field of view taken up by the obstruction is determined. This area is then multiplied by the depth of the detection portion 24 to obtain the volume of the obstruction, $V_{OBS}$. Here, the assumption that the obstruction spans the entire depth of the detection portion 24 is made. This volume, $V_{OBS}$, is then subtracted from the unobstructed volume associated with the field of view, $V_{FOV}$, to obtain a corrected volume associated with the field of view 26, $V_{FOV,C}$.

The above embodiment uses two steps at respective grid dimensions (first coarse, then fine) to combine efficient measuring time with good resolution of obstructed areas. In other embodiments, a single step with a single grid size, coarse or fine, is used, as a trade-off between resolution and processing time.

If no obstruction is detected in the field of view 26, then $V_{OBS}$=0 and $$V_{FOV,C} = V_{FOV}$$

If an obstruction is detected in the field of view 26, then $$V_{FOV,C} = V_{FOV} - V_{OBS}$$

Figure 11:
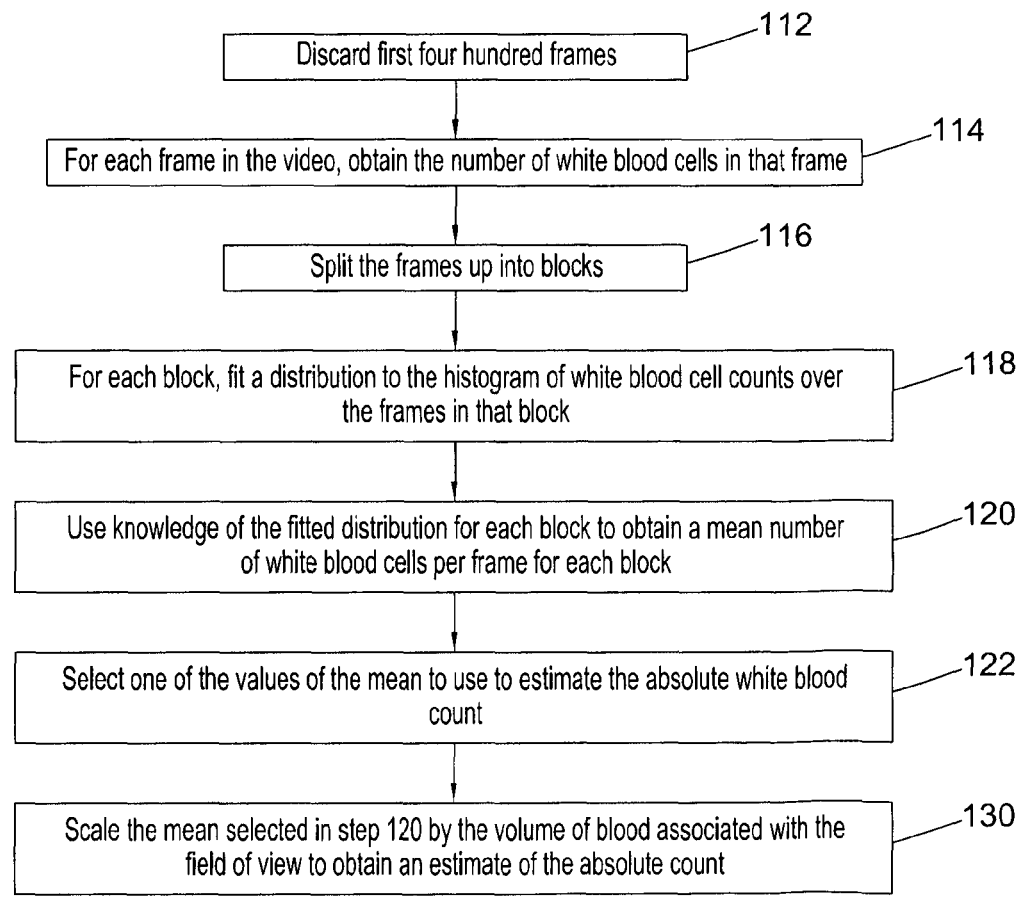
FIG. 11 illustrates a method for estimating the absolute white blood cell count by statistical analysis.

An estimate of the absolute white blood cell count is then determined at step 130 of FIG. 11 by scaling the estimated count to obtain a count per unit volume, for example by dividing the estimated number of cells per frame, by the volume of blood contained within a single frame, $V_{FOV,C}$.

Absolute Count Method 2—Speed Adaptive Sampling

In another embodiment, the absolute count of a blood sample is estimated by the direct averaging of counts contained within a subset of frames of the video of the blood sample to reduce the likelihood of double counting. A method of doing so is now described.

Within each frame taken of the blood sample is a small number of white blood cells and other objects, such as clusters of cells or platelets. Typically, there are between 1 and 10 objects in each frame, but frames can include 20-30 objects. As mentioned above, the image capture device 28 is set up to take approximately 17 frames per second and a given object will typically take 1-2 seconds to move across the field of view of the image capture device 28. Therefore, each object will appear in multiple frames.

Figure 13:
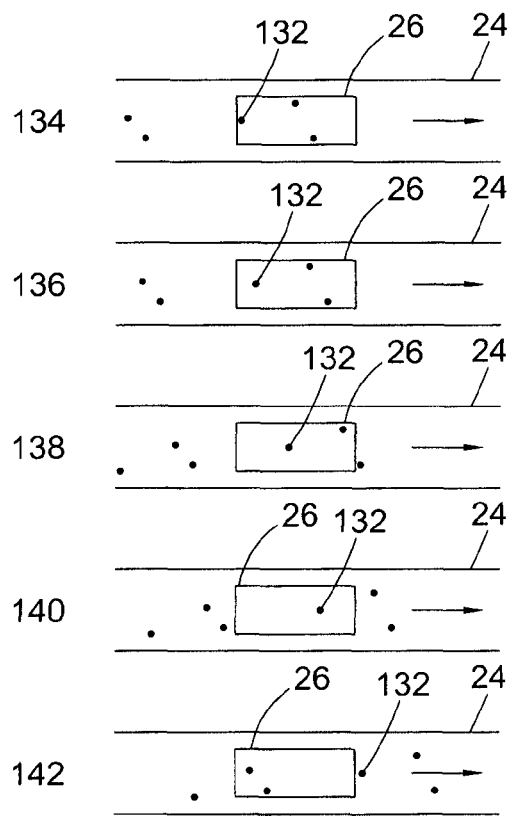
FIG. 13 shows a schematic view of a set of consecutive frames.

In some embodiments, the absolute white blood cell count is determined by selecting a subset of frames such that each object in the sample only appears once throughout the subset of frames, or at least such that the likelihood of double counting is reduced. With reference to FIG. 13, an object 132 moves across the field of view 26 of the image capture device 28 and is captured in frames 134-140. In frame 134, object 132 has just entered the field of view 26 of the image capture device 28 and in frame 142, object 132 has just left the field of view. The speed of an object 132 is estimated and used to determine which frame in the subset corresponds to frame 142, i.e. the first frame in the series of frames in which all of the objects captured in frame 134 are likely to have left the field of view and hence do not appear again.

Specifically, in some embodiments, the fastest speed of all object speeds moving across the field of view 26 in a frame n is used to select the next frame in the subset, frame, n+1.

Figure 14:
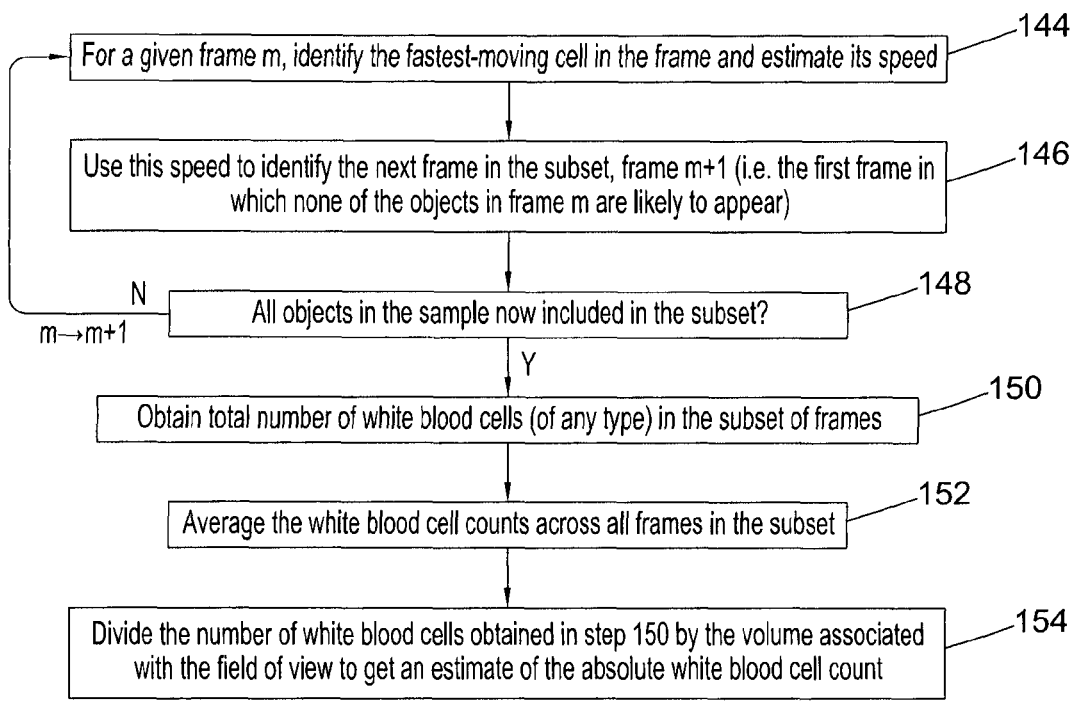
FIG. 14 illustrates a method for estimating the absolute white blood cell count by speed-adaptive frame sampling.

The process of estimating the absolute count is now described with reference to FIG. 14. At step 144, for a frame m, the fastest-moving cell in frame m is identified and its speed is estimated. This is done based on object positions from two or more of the current frame, previous or subsequent frames. At step 146, this speed is used to identify the next frame in which all of the objects are likely to have left the frame m. This next frame is selected as the next frame in the subset.

For a fastest object speed, v, in frame m, the next frame in the subset of frames, frame m+1, is determined by calculating the time interval between frames m and m+1. The time interval, t, is calculated using equation (3), below:

$$t = \frac{w}{v} \quad (3)$$

with w=diagonal extent of field of view, v=speed of fastest-moving object in frame m.

In some embodiments, the speed of the slowest-moving object is used to select the next frame in the subset. In this case, 'w' in equation (3) is the extent of the field of view along the direction of blood flow. In other embodiments, the average, for example the mean, or the median speed of all the objects in the frame is used to select the next frame in the subset. In this case, 'w' in equation (3) represents the diagonal extent of the field of view. In other embodiments, the average of the speeds of the fastest-moving object in each frame is estimated and is used to select the next frame in the subset.

Some embodiments make use of other speed measures to decide how to sub-sample the frames, for example based on an average speed across all frames and fixed sub-sampling rate or using a speed profile of frames with a corresponding variable sub-sampling rate. Equally, fastest and slowest speeds can be combined with various length scales (direction of scales, diagonal).

Steps 144-148 are repeated until, at step 148, it is determined that most or substantially all of the objects captured in the video appear in the subset of frames. In an embodiment, there may be a cut-off point, a frame number, for example, at which the selection of any further frames for the subset stops. In some embodiments, the selection of frames continues until the final frame in the set is reached, or the next frame that would be selected does not exist. In some embodiments, no further frames are selected beyond frames number 4300 (at 17 frames per second) or if flow speed falls below a certain threshold for a certain period of time or if flow stops completely.

At step 150, the white blood cells in each frame are identified as described above (step 112) and counted across all frames in the subset of frames.

At step 152, the white blood cell counts are averaged (or, in some embodiments, the median is calculated) across all frames in the subset. This estimated count is then scaled to obtain the estimated number of white blood cells per unit volume of blood at step 154. This is the absolute white blood cell count.

Absolute Count for Each of the White Blood Cell Types

Figure 15:
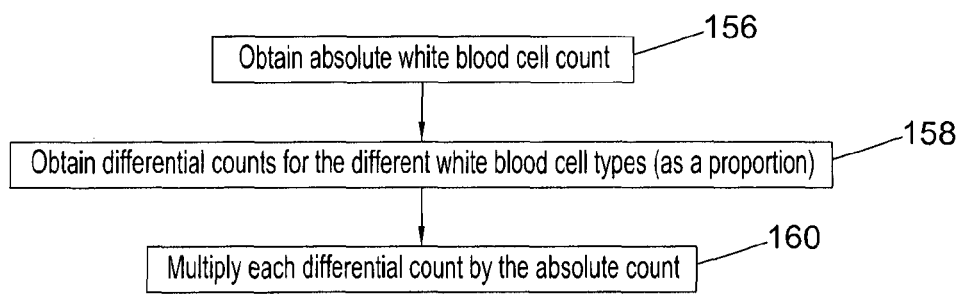
FIG. 15 illustrates a method for estimating absolute counts for each white blood cell type.

In some embodiments, the values of the differential counts and the value of the absolute white blood cell count are combined to obtain the absolute count for each of the five white blood cells types. A method of obtaining the absolute count for each white blood cell type is now described with reference to FIG. 15. At step 156, the absolute white blood cell count is obtained according to either of the methods above. At step 158, the differential count for each white blood cell type is obtained according to the method described above. At step 160, the absolute count for each white blood cell is obtained as a proportion of the total absolute white blood cell count in accordance with the respective differential counts. For example, each of the differential counts for each white blood cell type, rewritten as a proportion between 0 and 1 if not already in this form, is multiplied by the absolute white blood cell count to obtain an estimate of the absolute count for each white blood cell type.

Process Step Order

It will be appreciated that various combinations of the method steps as described above may be carried out and the order in which they are carried out may be altered to some extent without affecting the estimate of the counts.

In particular, it will be appreciated that various combinations of the processes (1) to (4) can be carried out. In one embodiment, processes (1) and (2) are carried out to obtain only the differential counts for the blood sample. Processes (1), (2) and (3) can be carried out in order to obtain both the differential counts and the absolute white blood cell count. As mentioned above, the differential and absolute counts can then be combined, in action (4), to obtain the absolute counts for each of the five white blood cell types.

It will also be appreciated that the steps of the processes described above do not necessarily have to be carried out in a certain order. The steps of the processes may be rearranged to some extent without affecting the one or more respective estimates of the one or more types of cell counts. For example, in one embodiment where only the differential counts are obtained, classification results for the objects in each of the frames are obtained and then the objects are tracked across multiple frames. In another such embodiment, the objects are first tracked across multiple frames and then classification results are obtained. For example, classification results for each object are only obtained in frames in which it is tracked. Since the tracking of some objects stops once they get too close to another object, it is useful, for the purposes of determining the differential counts, to only obtain classification results for an object in each frame in which it is tracked. The latter option, i.e. tracking the objects and then obtaining classification results, therefore allows a more efficient use of computing power as classification results are only obtained for the objects in the relevant frames.

Similarly, in an embodiment where the absolute white blood cell count is determined using the speed-adaptive sampling method, a subset of frames is selected such that the likelihood of each object in the sample appearing only once in the subset is increased. It is therefore only necessary to obtain classification results for the objects in the subset of frames. In one embodiment, the subset of frames is therefore selected before classification results for the objects in each frame are obtained so this is only done for the relevant objects. This allows for a more efficient use of computing power. It is equally possible however, to obtain classification results for the objects in each of the frames in the whole video before selecting the subset. This may be more efficient if the classification results are also used in other processes.

Obtaining classification results for each of the objects in each of the frames is useful for the statistical method of determining the white blood cell count. In this process, results may be obtained for every object and an object may be counted in all frames it appears in.

Further, in using either of the methods for determining the absolute white blood cell count, the objects only need to be classified as 'white blood cell' or 'non-white blood cell', whereas in the differential counts method, the type of each white blood cell must be determined. In determining the absolute white blood cell count only, a simpler classifier (of 'white blood cell' or 'non-white blood cell') can be used in some embodiments. An object may be classified as either 'white blood cell' or 'non-white blood cell' by summing all white blood cell class belonging scores for that object and making the classification of 'white blood cell' if the sum is greater than a threshold (for example 0.5 if the class belonging scores are probabilities).

In some embodiments in which objects are tracked across frames in order to determine an overall classification for the tracked objects (in the context of differential counts or otherwise), these overall classifications may be used in estimating the absolute counts. In tracking an object and determining an overall classification for that object, a list of object identifiers (assigned in step 46 of FIG. 3) which correspond to that object in the different frames in which it is tracked is obtained. Since these object identifiers correspond to the same object, they will have the same overall classification. When it comes to estimating the absolute counts, the white blood cells in a given frame may be identified by looking at the class belonging scores which were obtained as described above in the context of differential counts, that is by tracking. In other embodiments, an object may be classified as a white blood cell if it has an overall classification (as a result of combining classifications or classification scores over tracked frames) of any one of the white blood cells types. It will be appreciated that overall classifications may only be used in place of looking at the class-belonging scores for objects which are tracked, i.e. only for those objects for which an overall classification has been determined by tracking. Using the overall classifications where possible may be more accurate than looking at the class-belonging scores only as the overall classification is determined using the class-belonging scores from more than one frame.

In some embodiments, the tracking method described above may be used to determine an overall classification for at least some of the cells. These classifications may then be used to estimate the absolute counts only, the differential counts only or both.

Further Device Embodiments

It will be appreciated that, while specific embodiments of a device are described above, many variations are possible in various embodiments.

In the above embodiments, the sample flows through the connecting conduit 20 by capillarity. However, the flow of the sample through the connecting conduit 20 may equally be driven by a pressure difference or by any other means.

The microfluidic liquid handling structure as described above may be implemented on a 'lab on a disc' cartridge designed for rotation about an axis of rotation. Once the sample has been introduced into the microfluidic liquid handling structure 10, through the sample inlet 16, the sample inlet is sealed and the device is placed in an instrument comprising a rotation mechanism. In this embodiment, the image capture device may be integral to the instrument into which the cartridge is placed. The rotation mechanism allows angular positioning of the cartridge to be controlled. A positioning sensor may be used to assist the precise alignment of the detection portion 24 with the field of view 26 of the image capture device 28. The cartridge may also be immobilized or slowly rotating for discrete positioning purposes and all fluidic functions may be accomplished by capillary based handling of the blood sample without further interference/assistance. Once the cells in the sample have been classified according to an embodiment as described above, the cartridge may be rotated about an axis of rotation for the further processing of the same or a different sample within the device. Upon rotation of the cartridge about the axis of rotation, a liquid sample in the cartridge experiences a centrifugal force. An example of such a cartridge can be found in application WO2013135713, incorporated herein by reference.

In some embodiments, associated with each cartridge is the value of $V_{FOV}$ for that particular cartridge for use where necessary in the methods described above. For example, $V_{FOV}$, may be recorded on a machine readable element on the cartridge or may be stored elsewhere.

All of the fluidic structures described herein may be designed in polar coordinates relative to said axis of rotation. Consequently, all structures may be characterized by their radial and angular dimensions and positioning in respect of an axis of rotation.

As mentioned above, in some embodiments, the microfluidic liquid handling structure is provided on a cartridge. The cartridge, in some embodiments, in particular those using a rotational mechanism, resembles a CD/DVD configuration constituted by two transparent and planar circular halves brought together by an intermediate adhesive layer. The halves are preferably engraved with the microfluidic structures and openings to the exterior described above. With precise alignment of the microfluidic structures, the three parts may be assembled and bonded to form a self-contained cartridge.

It will be appreciated that the dimensions of the connection conduit 20, including its preparation and detection portions, and those of the loading 12 and waste 14 chambers may be adjusted.

Although the embodiments described above are adapted for the processing of a blood sample, at least some of the above embodiments are suitable for processing any liquid sample, for example any liquid to be reacted with one or more reagents prior to imaging, in which objects are to be counted.

The shape and length of the connection conduit 20 may be arranged in such a manner that enables space saving within the microfluidic liquid handling structure, for example using a meandering configuration. The trajectory of the connection conduit 20 may be provided within a single plane of the microfluidic liquid handling structure. It will be appreciated that although a straight connection conduit 20 is depicted in FIG. 1A, any shape suitable for providing a substantially planar trajectory of the blood flow within the microfluidic liquid handling structure could be provided.

It will be appreciated that other known reagents and combinations thereof may be used in the device. It will also be appreciated that the reagents may be arranged to have different dimensions in the preparation portion 22.

The described processes can be implemented using any suitable stand-alone or distributed computing environment using any suitable computing platform or processor, for example an integrated circuit, self-contained or in combination with other components of the system, a dedicated computing device housed on an appropriate card together with the other components of the system or otherwise, a standalone computing device such as a personal computer, tablet computer or mobile phone or a server which performs the necessary processes at least in part remotely exchanging data over a network connection. The processing may be implemented in a client-server architecture, with the processing being distributed between the client and the server in any appropriate manner. The client may include any of the above mentioned devices.

While specific embodiments have been described above for illustration, many variations, alterations and juxtapositions of the specific features in addition to those specifically mentioned above, will occur to the skilled reader upon reading the description and are within the scope of the present disclosure. The scope of the invention is defined by the appended claims.

Part II
Structure and Operation of Device

Figure 16:
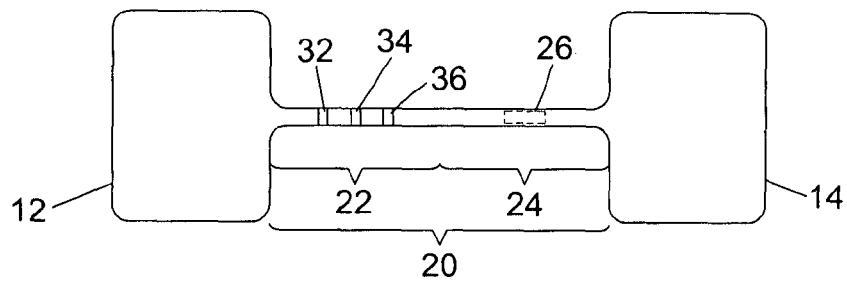
FIGS. 16a-c illustrate views of a microfluidic liquid handling structure.
Figure 16:
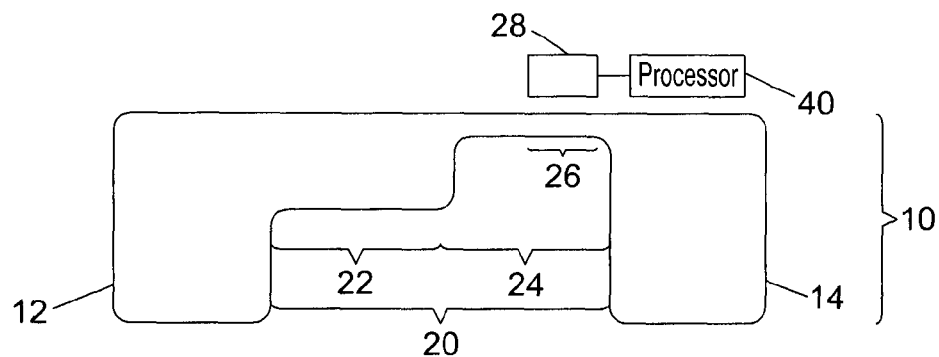
Figure 16:
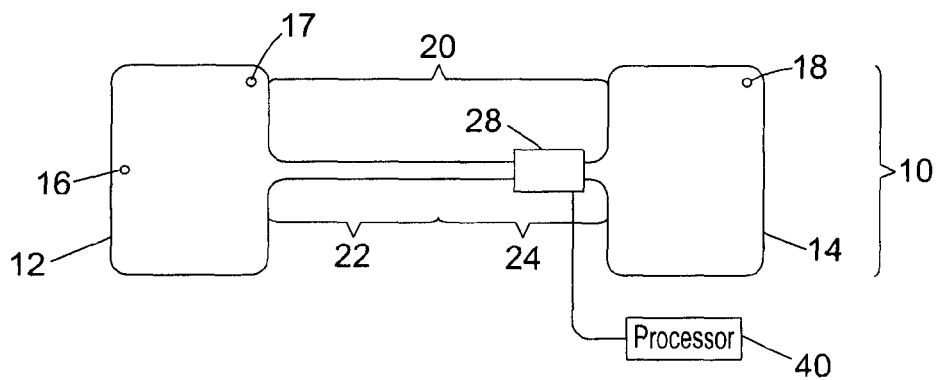

Referring to FIGS. 16A and 16B, a device 2, for the classification and counting of white blood cells within a blood sample is described. The device 2 includes a microfluidic liquid handling structure 10. FIGS. 16A and 16B illustrate mutually perpendicular cross-sections of the device 2, including the microfluidic liquid handling structure 10. FIG. 16C illustrates the device 2 as viewed from above.

With reference to FIG. 16C, the microfluidic liquid handling structure 10 comprises the following main elements: a loading chamber 12, a connection conduit 20 and a waste chamber 14. The loading chamber 12 has a sample inlet 16 through which a blood sample can be introduced into the microfluidic liquid handling structure 10. The inlet 16 is sealable in order to, when sealed, prevent the sample escaping once it is in the microfluidic liquid handling structure 10. The waste chamber 14 and the loading chamber 12 have air vents 17, 18 such that the chambers are open to the atmosphere. This allows the blood sample to flow from the loading chamber, through the conduit 20 and into the waste chamber 14 by capillary action. The microfluidic liquid handling structure forms part of a cartridge insertable into a holding structure for holding the cartridge relative to an image capture device 28. In some embodiments, the cartridge may come with a custom metering implement for metering an appropriate volume of blood for application to the microfluidic liquid handling structure, for example a pipette.

In some embodiments, the microfluidic liquid handling structure 10 is sealed from the atmosphere when the inlet 16 is sealed and the microfluidic liquid handling structure includes a network of air channels including an air circuit which connects the loading chamber 12 and the waste chamber 14. The air circuit allows air to escape from the waste chamber 14 into the loading chamber 12 as the blood sample flows from the loading chamber 12 and fills the waste chamber 14. The air circuit includes one or more flow barrier valves, for example a sudden expansion of the air circuit, to prevent the sample from entering the air circuit by capillarity.

Sharp angles within the microfluidic liquid handling structure 10 are preferably avoided to reduce impediments to sample flow and to prevent trapping of air bubbles inside the connection conduit 20 whilst the waste chamber 14 is filling with the blood sample. The connection conduit 20 comprises two portions: a preparation portion 22 and a detection portion 24. The preparation portion 22 is arranged for the lysing of red blood cells and staining of white blood cells. As the sample moves through the preparation portion 22, it encounters a series of patches of dry reagents 32, 34, 36. Although in FIG. 16A three patches of dry reagents are provided, it will be appreciated that any number (one or more) patches may be provided within the preparation portion 22. As the blood sample flows over the one or more patches, it will dissolve the reagent(s) which will gradually diffuse through the blood volume and prompt a chemical reaction. The dynamics of such reactions depends mainly on the blood flow rate and the length(s) of the patch(es) of dry reagent. The content of dry reagent stored in the preparation portion 22 and how easily it dissolves in blood will also have an effect on the dynamics. The dry reagents comprise, for example, a haemolytic agent for the selective lysing of red blood cells and a staining agent for differential staining of white blood cells. A staining agent from the family of hematoxylin and eosin (H&E) stains, Romanowsky stains, methacromatic stains or any combination thereof can be used. From combinations of colour information with morphological features like granularity, size, shape of the cell cytoplasm and nucleus, it is then possible to obtain a set of distinct signatures for each of the sub-populations under study. Further discussion of the use of reagents can be found in application WO2013135713, which is incorporated herein by reference.

In one specific embodiment, the preparation portion 22 contains a series of 2 sequential reagents, comprising a first reaction site which is 10 mm long comprising a mixture of surfactant and lytic agent (Surfynol and saponine, respectively) and a 10 mm long reaction site with a mixture of stains. In this embodiment, the mixture of stains includes a mixture of eosin, methylene blue and basic orange 21 leading to differential colours for a 5-part classification of white blood cells: lymphocytes stain blue, monocytes stain blue/purple, neutrophils exhibit blue nucleus and pale yellow cytoplasm, eosinophils exhibit blue nucleus and dark yellow granules, basophils stain bright pink.

The detection portion 24 of the connection conduit 20 is where the cells are, in operation, imaged and counted. The detection portion 24 is aligned with a field of view 26 of an image capture device 28, such that the blood flowing through the detection portion 24 flows across the field of view 26 of the image capture device 28. Approximately two thirds of the width of the detection portion 24 is within the field of view 26 of the image capture device 28. The image capture device 28 is positioned above the detection portion 24. The image capture device 28 includes a lens arrangement and a focusing mechanism for focusing on the blood sample flowing into the detection portion 24 to image the lysed and stained sample when it is in the detection portion 24.

The detection portion 24 is arranged to be shallower than preparation portion 22, such that it accommodates a single layer of objects which move across the field of view 26 of the image capture device 28. It is preferable to ensure that a single layer of objects move across the field of view of the image capture device 28 to increase the chance that each object is counted and to facilitate the classification of the objects. If multiple layers of objects were provided in the field of view then some objects could be blocked from view completely and others could be partially obscured by other objects. Having a single layer of objects also facilitates any defining characteristics of objects (including cells) being captured. The preparation portion 22 is deeper than the detection portion 24 to facilitate the arrangement of the reagents 32, 34, 36 and to increase their surface areas. The reduction in depth from the preparation portion 22 to the detection portion 24 facilitates sample flow by capillarity through the preparation portion 22 and the detection portion 24. Further, the depth of the preparation portion facilitates homogeneity of lysis and staining of the blood cells.

Figure 17:
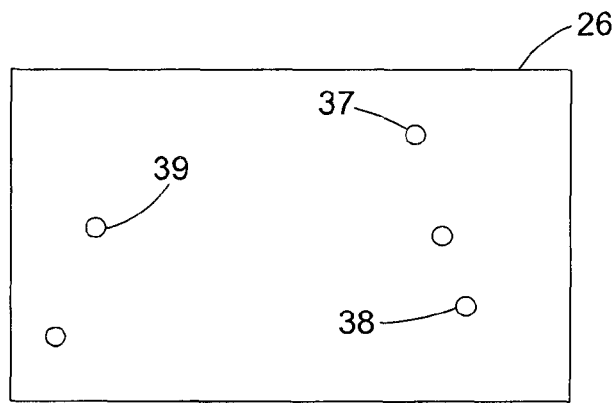
FIG. 17 illustrates a schematic view of white blood cells in the detection portion.

In some embodiments, the detection portion 24 is at least twice as wide as the estimated largest dimension of any object to be detected and its depth is less than twice this largest dimension. In one embodiment, the detection portion 24 is 15 mm long, 0.06 mm wide and 0.02 mm deep. This configuration defines a volume for the detection portion 24 of 0.018 pt. FIG. 17 schematically illustrates the type of image obtained with several stained white blood cells 37, 38, 39 in such a detection portion.

Associated with the device 2 is a processor 40 configured to carry out the data processing required to obtain the cell counts. The processing steps will be described below.

The operation of the device 2 will now be described. The sample is introduced into the microfluidic liquid handling structure 10 through the inlet 16 and the inlet is then sealed. The sample enters the loading chamber 12 and is drawn by capillary action into the preparation portion 22, and, subsequently, into the detection portion 24. Therefore, once the blood sample enters the detection portion 24, it has already reacted with the red blood cell lytic agent and differential stains for white blood cells.

The image capture device 28 may initially be out of focus, but when the sample enters the detection portion 24 and subsequently the field of view of the image capture device 28, a focusing mechanism focuses the image capture device 28 on the sample and the image capture device 28 begins capturing images as frames of a video. Focusing methods, implemented in software and/or hardware are generally well known. A specific example adapted for use with the device 2 is disclosed in UK application number 1417170.6 incorporated herein by reference. In one specific implementation, the video is taken for four minutes at a rate of 15 frames per second, resulting in approximately 15-30 frames being captured of each cell. Frame acquisition durations and rates are adapted to the specific flow in the microfluidic liquid handling structure 10 to capture a sufficient number of frames per cell for subsequent analysis. Durations and times are readily adapted by a skilled person to optimise data collection according to the circumstances. During the assay, approximately 1500 cells move across the field of view 26 of the image capture device 28 in one example, for a healthy sample. The data obtained from the video consists of a series of frames (approximately 4000), wherein each frame comprises an image containing one or more cells and other objects, such as clusters of cells or platelets. Some frames may contain no objects at all and these frames are discarded.

Having described a device used for various cell counting processes, such processes are now described in detail.

Object Classification

A method used to classify the objects in a frame is now described with reference to FIG. 18. Each frame is first segmented into object and background pixels at step 42 using thresholding in some embodiments, for example Otsu's method, and the objects in the frame are identified at step 44, as is well known in the art of image processing. At step 46, each object is given an identifier which is unique to that object and frame and at step 48, a list of the object identifiers and their associated object positions is obtained. Image patches centred on the object positions are extracted at step 50. Then, for a first image patch, the image patch is segmented into separate object regions at step 52. These regions are, in overview: background; nucleus of the cell; cytoplasm.

In some embodiments, a k-means clustering algorithm based on RGB colour values is used for segmentation. The pixels of each image patch are clustered using k-means (or any other suitable clustering algorithm) on the RGB values of the pixels to define three clusters. This results in a mask with a cluster identifier (cluster 1, cluster 2, cluster 3) for each pixel. The cluster with the darkest (e.g. average) pixel intensity or colour is labelled as the nucleus, the cluster with the lightest (e.g. average) pixel intensity or colour is labelled as background and the remaining cluster is labelled as cytoplasm. The segmentation algorithm therefore outputs three regions, which are identified as background, nucleus and cytoplasm according to the intensity or colour of each region.

In some embodiments, as a refinement, k-means clustering used again to split pixels previously identified as the nucleus, to cluster these pixels into two sub-regions: nucleus and 'cytoplasm region 2'. This may help to more accurately define the boundary between the nucleus and cytoplasm. In this step, pixels labelled as nucleus are either left as 'nucleus', or are reclassified as 'cytoplasm region 2'.

In some embodiments, an alternative segmentation approach can be applied, which advantageously may be more robust against image variations. The approach involves the following steps for each image patch:
1) k-means clustering with k=2 to separate cell (darker pixels) from background (lighter pixels);
2) label background pixels as background and mask (set to a predefined colour, say green);
3) k-means clustering with k=3 to get nucleus (darkest), cytoplasm (lighter) and the now, say, green background;
4) label cytoplasm pixels as cytoplasm region 1 and mask cytoplasm in addition to the background by setting cytoplasm pixels to the predefined colour;
5) k-means clustering with k=3 to get nucleus pixels (darkest), cytoplasm region 2 and the now masked background (which now includes the previous cytoplasm region 1 area);
6) label nucleus pixels as nucleus and cytoplasm region 2 pixels as cytoplasm region 2.

In embodiments where only one cytoplasm region is segmented, the clustering stops after step 3 with labelling the nucleus and cytoplasm pixels accordingly.

In some embodiments, the 'cytoplasm region 2' region is merged with the cytoplasm identified in the first pass ('cytoplasm region 1') and labelled as an overall cytoplasm for the further analysis/cell classification. In other embodiments, 'cytoplasm region 1' is taken as representative of the cytoplasm. Noting that 'cytoplasm region 2' is a transition region between the nucleus and cytoplasm of the cell, object parameters for this region are used in classifying objects in addition to the overall cytoplasm, in some embodiments.

Overall, each object is split into three or four regions, depending on the embodiment: nucleus; background; cytoplasm; cytoplasm region 2, or: nucleus; background; cytoplasm.

Examples of other clustering based algorithms for identifying blood cells can be found in 'White Blood Cell Segmentation by Color-Space-Based K-Means Clustering', Congcong Zhang et al, Sensors 2014, 14, 16128-16147; doi:10.3390/s140916128; 'Leukocyte segmentation and classification in blood-smear images', Herbert Ramoser et al, Proceedings of the 2005 IEEE Engineering in Medicine and Biology 27th Annual Conference, Shanghai, China, Sep. 1-4, 2005, all incorporated herein by reference, and may be used for object segmentation in some embodiments. It will be understood that any other suitable segmentation method, supervised or unsupervised, using clustering or other techniques, may be used in some embodiments. Specifically, any suitable alternative clustering algorithm other than k-means may be used in any of the above embodiments.

For objects which are not cells and hence do not have a nucleus or cytoplasm, the k-means algorithm still splits the object up into multiple regions but these regions are not meaningful and the convergence of the k-means algorithm is not as good for non-cell object as that for cells. Non-cell objects are identified by the classifier discussed below.

At step 54, object parameters are extracted from each image patch for each of the respective objects. These parameters include:
  image saturation averaged over the relevant pixels and its standard deviation
  intensity averaged over the relevant pixels and its standard deviation,
  colour averaged over the relevant pixels and its standard deviation,
  object roundness, $$\text{compactness} = 2\frac{\sqrt{\pi * \text{object area}}}{\text{object perimeter}},$$

for example $$\text{form factor} = \frac{4\pi * \text{object area}}{(\text{object perimeter})^2},$$

for example
  object perimeter,
  object area and
  focus quality of the image.

FIG. 19 shows a list of object parameters that may be extracted for each of the respective objects.

The values of some parameters are extracted for the object as a whole, for example the object roundness and the object perimeter. The values of other parameters are extracted for each object region, for example the intensity and colour and their standard deviations, using masks to isolate each region in turn. The values for the background region are used for calibration. For example, they are used to account for more staining in one region of the field of view 26 than another. If the focus quality of an image is too poor, for example if it is below a predetermined threshold, then that image is discarded.

At step 56, the values of the extracted parameters are then used with a Logistic Model Tree classifier to obtain classification results, a discussion of which may be found in N. Landwehr, M. Hall and E. Frank, 'Logistical Model Trees', Machine Learning, vol. 59, pages 161-205, 2005, incorporated herein by reference. The Logistic Model Tree is trained prior to its use for classification using expert labelled training data. The Logistic Model Tree is used to obtain class-belonging scores for each object, e.g. probabilities of each object belonging to each object type. In some embodiments, the SimpleLogistic class provided by the Weka collection of machine learning algorithms is used (see, Class SimpleLogistic by Authors Niels Landwehr and Mark Sumer; Weka 3: Machine Learning Software in Java, both incorporated by reference herein and available online). Any suitable classifier, for example a Support Vector Machine can be used, as will be apparent to a person skilled in the art. Steps 52-56 are repeated for each object in the frame.

The object types include five white blood cell types, nine other object types, used for objects other than white blood cells to be counted, and a 'cell cluster' classification. The object types are:
  lymphocyte
  monocyte
  neutrophil
  basophil
  eosinophil
  'unstained cell'
  'cluster of cells'
  'background object'
  'large debris' (e.g. aggregate of platelets, undissolved stain)
  'out-of-focus cell'
  'red blood cell'

'nucleated red blood cell'
'out of range'
'other'
'eosinophil within a cluster'

The above object types or classes are largely self-explanatory. 'Out of range' refers to objects that do not lie entirely within the frame and hence only part of the object can be seen. 'Other' refers to any debris that does not fall into one of the other classifications.

If a blood sample contains too many objects in any one of the non-white blood cell (i.e. other than the first five) classifications (for example if the proportion of objects classified as an 'other' type exceeds a threshold) then the results of the assay may be discarded.

The 'eosinophil within a cluster' classification is useful because eosinophils make up a very small proportion of all white blood cells. If those eosinophils contained in a cluster of cells were ignored and not counted, then very few or even no eosinophils would be counted in a given assay.

Clusters of cells are identified by the classifier, as above. Typically, a cluster of cells is characterised by a large object area, for example 500 pixels or more. Therefore, object area is discriminative of clusters of cells. An eosinophil has a distinct colour signature and as such, the mean colour of the cluster as a whole is shifted. By identifying this shift in colour, the presence of an eosinophil within a cluster is detected. As detecting an eosinophil within the cluster is a relatively rare event, in contrast to detecting other objects, it is assumed that if the shift in colour of the cluster is detected, that the cluster contains one eosinophil, in some embodiments. Further processing to count eosinophils in identified clusters is used in other embodiments. Any of the above method steps may be carried out by or under the control of a processor.

Including a cell within a cluster in estimating a cell count can be implemented alone or in combination with other disclosed features and steps. This technique may also be applied to other cell types, for example Basophils.

In some embodiments, the object is classified as the class for which the object has the highest class-belonging score. In some embodiments, if the highest class-belonging score is below a threshold, the object is classified as 'unknown'.

Figure 18:
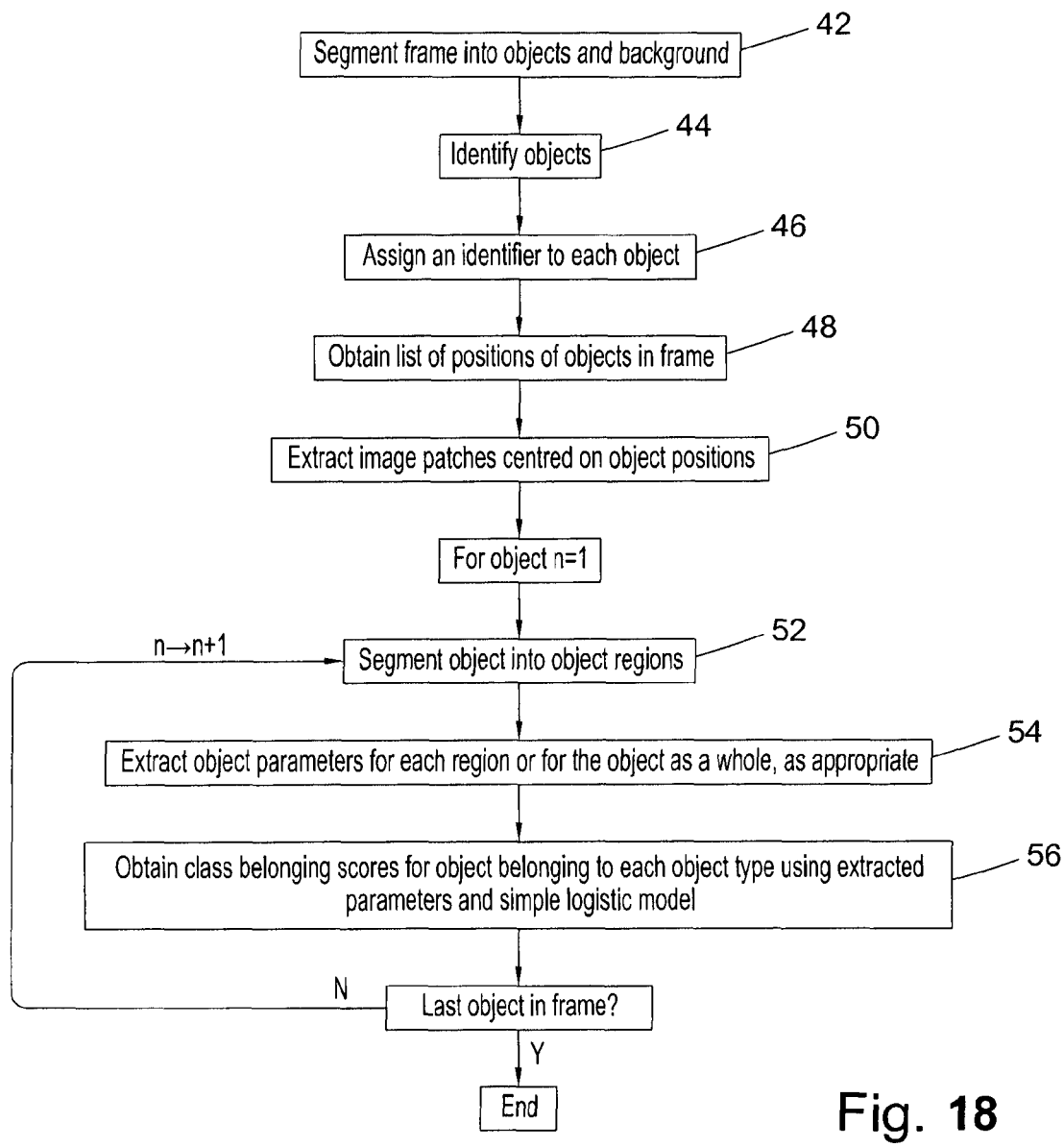
FIG. 18 illustrates a flow diagram representing a method for obtaining classification results for objects within a frame.

The process described with reference to FIG. 18 is repeated for as many frames as necessary.

Cell Tracking

Figure 20:
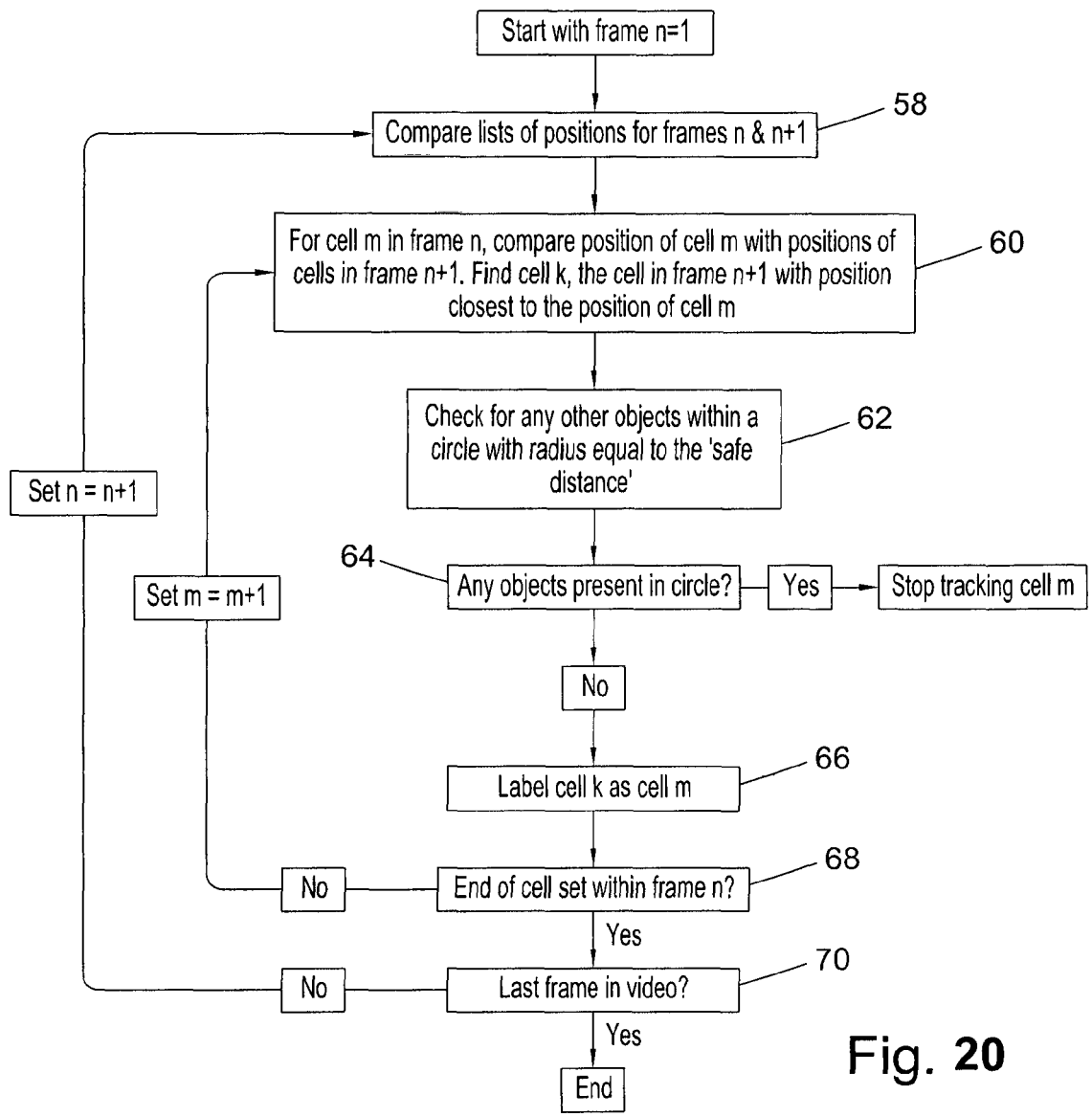
FIG. 20 illustrates a method for tracking objects across multiple frames.

As mentioned above, in some embodiments, an estimate of the absolute count for a blood sample may be determined by selecting a subset of the frames captured based on an estimate of cell velocity. One way to estimate cell velocities is by tracking cells from one frame to the next. This process will now be described with reference to FIG. 20.

Figure 21:
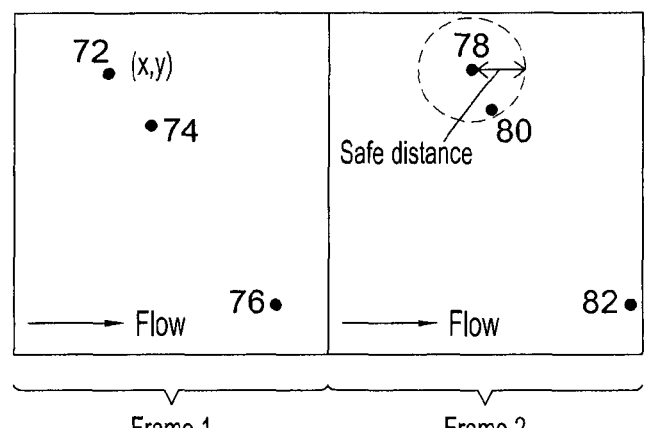
FIG. 21 illustrates two consecutive frames of the blood sample.

Having obtained a list of object positions during the classification of the objects, as described above, the list of object positions for frame 1 is compared to the list of object positions for frame 2 at step 58. For a first object 72 (see FIG. 21) at position (x, y) in the first frame, an object 78 in a second frame which has the position closest to position (x, y) is identified. At step 62, a check is carried out to determine whether any other objects lie within a circle centred on object 78, with radius equal to a predefined 'safe distance'. This 'safe distance' is defined as a distance at which two objects are too close to be distinguishable with confidence from each other from one frame to the next. At step 64, if an object 80 is within the safe distance from object 78 then object 72 cannot be identified in frame 2 and the tracking of object 72 stops. If at step 64, no objects within the safe distance from object 78 are found, object 78 is identified as being the same object as object 72 in the previous frame. Steps 60-68 are repeated for all objects in the first frame such that each object is either tracked from frame 1 to frame 2, or cannot be identified with enough certainty in frame 2. In the latter case (conflicting object within safe distance), the tracking of these objects stops. The process then moves onto the next frame, at step 70, and the lists of positions for frames 2 & 3 are compared. Steps 58-70 are repeated for all frames in the data set until lastly, the lists of object positions for frames n−1 and n are compared, where the data set consists of n frames.

In some embodiments, object velocity is used to improve tracking. For example, rather than picking the object 78 in frame 2 that is closest to object 72 in frame 1 at step 60, the object closest to the predicted position of object 72, based on the velocity of object 72 determined from frame 1 and one or more previous frames, is picked, which enables a reduction of the safe distance, since more information is used in the tracking. This is carried out, in some embodiments, in the tracking of an object from a second to a third frame and for subsequent frames thereafter, but not from a first to a second frame, because the velocity of the object is estimated by analysing more than one frame.

In tracking the objects, a set of image patches for each tracked object is obtained. In other words, the objects (image patches) obtained in the method described above with reference to FIG. 18 are 'matched up' with other objects (image patches) which correspond to the same object.

The dimensions of the field of view of the image capture device are known and based on these dimensions, the distance travelled by each object between frames is estimated. The time between frames is also known. Using this and the estimate of the distance travelled by an object between frames, an estimate of an object's velocity is determined.

Absolute Count Method 1—Statistical Analysis

As mentioned above, the absolute white blood cell count is the estimated number of white blood cells per unit volume of blood. Although the total volume of the blood sample used in the assay is not accurately known, the volume of blood which is within the field of view of the image capture device 28 at any one time is the product of the area of the field of view and the depth of the detection portion 24. This fact is used in estimating the absolute count.

The above means that the depth of the detection portion is such that all objects flowing through the detection portion can be imaged by the image capture device. This will be the case where the depth is of the order of white blood cell sizes, for example less than twice the largest cell dimension. If the detection portion is deeper than that, the depth of the detection portion is, in some embodiments, replaced by the depth of focus of the image capture device, throughout which all objects flowing through the corresponding cross-section can be imaged, for the purpose of calculating the volume of blood which is within the field of view of the image capture device 28 at any one time.

In an embodiment, the absolute white blood cell count is estimated using a statistical analysis. This process of estimating the absolute white blood cell count is described with reference to FIG. 22.

At step 84, the first four hundred frames in the set of frames obtained in taking the video of the blood sample are discarded. This is because these first four hundred frames typically contain a significant amount of debris, such as platelets.

At step 86, the white blood cells in each frame are identified and counted in each frame. In classifying the objects, class-belonging scores are obtained for the objects according to the method above. An object is counted as a white blood cell if it has a highest class belonging score for one of the five types of white blood cell. Alternatively, objects classified for counting purposes as white blood cells by summing all white blood cell class belonging scores and making the classification if the sum is greater than the sum of scores for the objects being of a non-leukocyte type (or a fixed threshold, for example 0.5 if the scores are probabilities).

At step 88, the remaining set of frames is split up into blocks, where each block contains approximately 1200 frames. Block 1 contains the first one thousand two hundred frames, block 2 contains the second one thousand two hundred frames and so on. At step 90, for each block, a Gamma distribution with parameters α and β is fitted to the distribution (histogram) of white blood cell counts from each frame in that block. A goodness of fit measure for each fit is obtained. The mean cell count per frame within each block, μ, is then found at step 92 as:

$$\mu = \alpha\beta \quad (1)$$

where α, β are the parameters of the Gamma distribution fitted to the count data of the respective block.

In another embodiment, a Poisson distribution with parameter λ (corresponding to the count per frame expected under the distribution) is fitted to the distribution (histogram) of white blood cell counts across the frames in each block and as before, a goodness of fit measure is obtained. The mean cell count per frame within each block is taken to be the parameter λ of the Poisson distribution.

At step 94, the value of the mean determined for one of the blocks is selected to be used to determine the overall estimate of the absolute white blood cell count. The value of the mean itself and the corresponding goodness of fit of the distribution is taken into account when choosing which value to use. As a starting point, the value of the mean for the first block of frames is considered. If a subsequent block has a better goodness of fit measure and the value of the mean for that block is not significantly lower than that of the first block (it is within 10% of the value for the first block, for example), then the value of the mean from that subsequent block is used to determine the overall estimate of the absolute white blood cell count. For example, if the value for the second block is similar to the value corresponding to the first block, for example it is only slightly lower, but the second value has a better goodness of fit measure, then the value for the second block is used. A value of a mean may be determined to be 'similar' to another value if it is within 10% of it, for example. If no such subsequent block with a better goodness of fit measure and a similar mean exists, the value of the mean from the first block is used. In obtaining an estimate of the mean cell count from a distribution fit to a block of frames in this way, it is advantageous to fit the distribution to frames over which the rate of flow of the blood sample is substantially constant. A substantially constant flow rate means that every object is likely to appear in approximately the same number of frames. Conversely, a variable flow rate would result in slow-moving cells appearing in many frames and faster-moving cells appearing in relatively few frames. To increase the likelihood of the flow being substantially constant over the frames to which a distribution is fitted, frames with an average object speed below a threshold are discarded, in some embodiments. For example, objects are tracked across frames, as described above, and the average object speed in each frame evaluated. Any frames for which the average object speed is below a predetermined threshold are then discarded and not considered in estimating the mean number of white blood cells per frame.

In some embodiments, additionally or alternatively, the dimensions and configuration of the microfluidic structure can be designed such that the rate of flow of blood sample through the detection portion can be considered substantially constant after a certain period of time has elapsed since the blood sample first reaches the detection portion, for example three seconds. A block of frames could then be selected, for the purpose of estimating the mean cell count per frame, which only includes frames after this time period has elapsed. In yet further embodiments, flow may be monitored otherwise and frames with too slow a flow, or blocks of flames with flow variability of flow speed above a threshold, discarded.

Having obtained an estimate of the mean cell count per frame, an estimate of the overall absolute white blood cell count is then obtained. The absolute count is based on both the mean (estimated) count and a blood volume associated with the count. The volume of blood 'captured' in a single frame, i.e. the volume of blood that is contained within the field of view of the image capture device 28, referred to as $V_{FOV}$, can be calculated using equation (2):

$$V_{FOV} = d * w * h \quad (2)$$

where d=depth of the detection portion 24, w=width of the field of view of the image capture device 28 along the direction of blood flow, and h=height of the field of view, i.e. the depth of the detection portion in the extent of the field of view across the detection portion 24, as discussed above.

Figure 23:
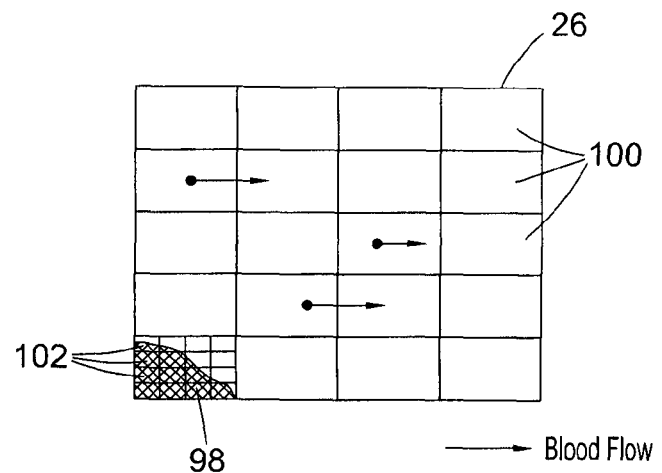
FIG. 23 shows a schematic diagram of the field of view of the image capture device split up into regions for the purpose of correcting for an obstruction.

In some embodiments, the value of $V_{FOV}$ is calculated online based on the dimensions of the detection portion, as described above. In other embodiments, information relating to $V_{FOV}$ may be part of a set of calibration data that comes with the microfluidic liquid handling structure 10, for example with on a cartridge on which the microfluidic liquid handling structure is provided, or with a tag readable by the device 2 attached to the cartridge or packaging containing the microfluidic liquid handling structure 10. In some embodiments, the accuracy of the determination of $V_{FOV}$ is verified by carrying out a check for any obstructions in the field of view. With reference to FIG. 23, examples of such obstructions could be an aggregate of platelets or cells or an air bubble. Such an obstruction 98 with volume $V_{OBS}$, in the field of view 26 would mean that the volume associated with the field of view is not entirely filled with blood. This would lead to an overestimation of the volume of the blood sample and hence an underestimation of the absolute white blood cell count.

To overcome this problem, a check is carried out for any such obstructions. This is done by splitting the field of view up into regions 100. The average number of objects passing through each region in a given time is recorded. If the average number of objects for any region is less than a certain threshold, then it is determined that there is an obstruction in that region. That region is then split up into further sub-regions 102, each comprising a small number of pixels. The pixels within the obstructed volume will have no objects passing across them and so by identifying these pixels with zero passing objects, the area of the field of view taken up by the obstruction is determined. This area is then multiplied by the depth of the detection portion 24 to obtain the volume of the obstruction, $V_{OBS}$. Here, the assumption that the obstruction spans the entire depth of the detection portion 24 is made. This volume, $V_{OBS}$, is then subtracted from the unobstructed volume associated with the field of view, $V_{FOV}$, to obtain a corrected volume associated with the field of view 26, $V_{FOV,C}$.

The above embodiment uses two steps at respective grid dimensions (first coarse, then fine) to combine efficient measuring time with good resolution of obstructed areas. In other embodiments, a single step with a single grid size, coarse or fine, is used, as a trade-off between resolution and processing time.

If no obstruction is detected in the field of view 26, then $V_{OBS}=0$ and $$V_{FOV,C}=V_{FOV}$$

If an obstruction is detected in the field of view 26, then $$V_{FOV,C}=V_{FOV}-V_{OBS}$$

Figure 22:
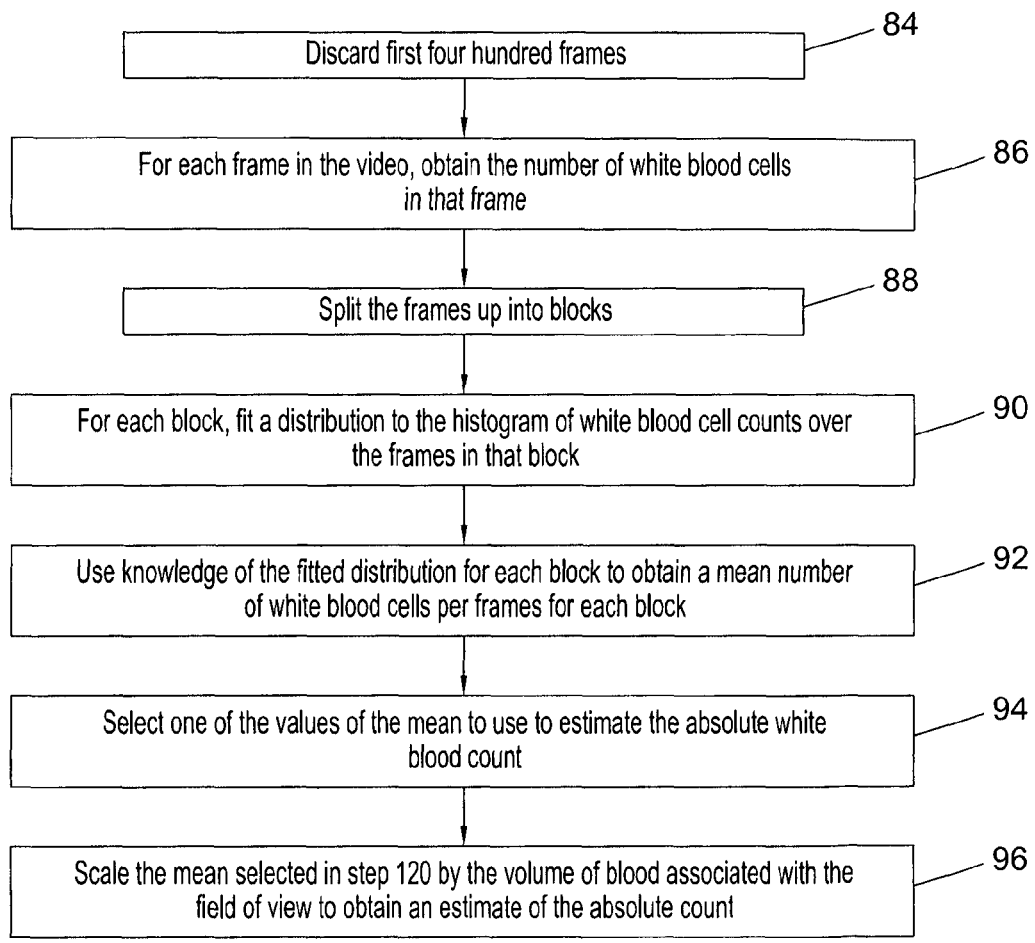
FIG. 22 illustrates a method for estimating the absolute white blood cell count by statistical analysis.

An estimate of the absolute white blood cell count is then determined at step 96 of FIG. 22 by scaling the estimated count to obtain a count per unit volume, for example by dividing the estimated number of cells per frame, by the volume of blood contained within a single frame, $V_{FOV,C}$.

Absolute Count Method 2—Speed Adaptive Sampling

In another embodiment, the absolute count of a blood sample is estimated by the direct averaging of counts contained within a subset of frames of the video of the blood sample to reduce the likelihood of double counting. A method of doing so is now described.

Within each frame taken of the blood sample is a small number of white blood cells and other objects, such as clusters of cells or platelets. Typically, there are between 1 and 10 objects in each frame, but frames can include 20-30 objects. As mentioned above, the image capture device 28 is set up to take approximately 17 frames per second and a given object will typically take 1-2 seconds to move across the field of view of the image capture device 28. Therefore, each object will appear in multiple frames.

Figure 24:
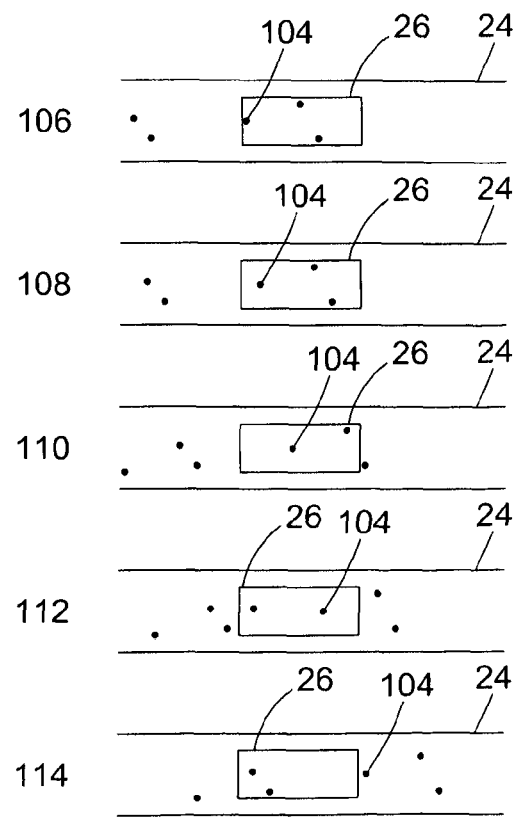
FIG. 24 shows a schematic view of a set of consecutive frames.

In some embodiments, the absolute white blood cell count is determined by selecting a subset of frames such that each object in the sample only appears once throughout the subset of frames, or at least such that the likelihood of double counting is reduced. With reference to FIG. 24, an object 104 moves across the field of view 26 of the image capture device 28 and is captured in frames 106-112. In frame 106, object 104 has just entered the field of view 26 of the image capture device 28 and in frame 114 object 104 has just left the field of view. The speed of an object 104 is estimated and used to determine which frame in the subset corresponds to frame 114, i.e. the first frame in the series of frames in which all of the objects captured in frame 106 are likely to have left the field of view and hence do not appear again.

Specifically, in some embodiments, the fastest speed of all object speeds moving across the field of view 26 in a frame n is used to select the next frame in the subset, frame, n+1, having obtained estimates of object velocities either by tracking objects over multiple frames or by assuming that cell velocities are the same and equal to the velocity of the blood sample through the detection portion.

Figure 25:
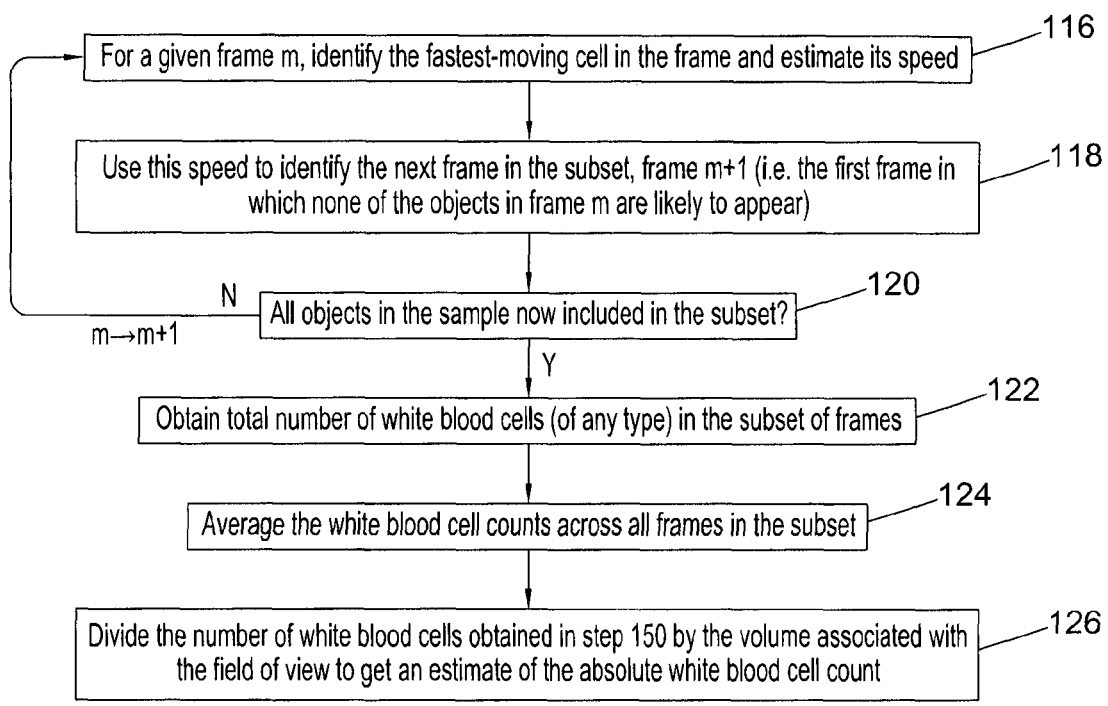
FIG. 25 illustrates a method for estimating the absolute white blood cell count by speed-adaptive frame sampling.

The process of estimating the absolute count is now described with reference to FIG. 25. At step 116, for a frame m, the fastest-moving cell in frame m is identified and its speed is estimated. This is done based on object positions from two or more of the current frame, previous or subsequent frames. At step 118, this speed is used to identify the next frame in which all of the objects are likely to have left the frame m. This next frame is selected as the next frame in the subset.

For a fastest object speed, v, in frame m, the next frame in the subset of frames, frame m+1, is determined by calculating the time interval between frames m and m+1. The time interval, t, is calculated using equation (3), below:

$$t = \frac{w}{v} \qquad (3)$$

with w=diagonal extent of field of view, v=speed of fastest-moving object in frame m.

In some embodiments, the speed of the slowest-moving object is used to select the next frame in the subset. In this case, 'w' in equation (3) is the extent of the field of view along the direction of blood flow. In other embodiments, the average, for example the mean, or the median speed of all the objects in the frame is used to select the next frame in the subset. In this case, 'w' in equation (3) represents the diagonal extent of the field of view. In other embodiments, the average of the speeds of the fastest-moving object in each frame is estimated and is used to select the next frame in the subset.

Some embodiments make use of other speed measures to decide how to sub-sample the frames, for example based on an average speed across all frames and fixed sub-sampling rate or using a speed profile of frames with a corresponding variable sub-sampling rate. Equally, fastest and slowest speeds can be combined with various length scales (direction of scales, diagonal).

Steps 116-120 are repeated until, at step 120, it is determined that most or substantially all of the objects captured in the video appear in the subset of frames. In an embodiment, there may be a cut-off point, a frame number, for example, at which the selection of any further frames for the subset stops. In some embodiments, the selection of frames continues until the final frame in the set is reached, or the next frame that would be selected does not exist. In some embodiments, no further frames are selected beyond frame number 4300 (at 17 frames per second) or if flow speed falls below a certain threshold for a certain period of time or if flow stops completely.

At step 122, the white blood cells in each frame are identified as described above and counted across all frames in the subset of frames.

At step 124, the white blood cell counts are averaged (or, in some embodiments, the median is calculated) across all frames in the subset. This estimated count is then scaled to obtain the estimated number of white blood cells per unit volume of blood at step 126. This is the absolute white blood cell count.

Process Step Order

It will be appreciated that various combinations of the method steps as described above may be carried out and the order in which they are carried out may be altered to some extent without affecting the estimate of the counts. In an embodiment where the absolute white blood cell count is determined using the speed-adaptive sampling method, a subset of frames is selected such that the likelihood of each object in the sample appearing only once in the subset is increased. It is therefore only necessary to obtain classification results for the objects in the subset of frames. In one embodiment, the subset of frames is therefore selected before classification results for the objects in each frame are obtained so this is only done for the relevant objects. This allows for a more efficient use of computing power. It is equally possible however, to obtain classification results for the objects in each of the frames in the whole video before selecting the subset. This may be more efficient if the classification results are also used in other processes.

Obtaining classification results for each of the objects in each of the frames is useful for the statistical method of determining the white blood cell count. In this process, results may be obtained for every object and an object may be counted in all frames it appears in.

Further, in determining the absolute white blood cell count, the objects only need to be classified as 'white blood cell' or 'non-white blood cell'. Therefore, a simpler classifier (of 'white blood cell' or 'non-white blood cell') can be used in some embodiments. An object may be classified as either 'white blood cell' or 'non-white blood cell' by summing all white blood cell class belonging scores for that object and making the classification of 'white blood cell' if the sum is greater than a threshold (for example 0.5 if the class belonging scores are probabilities).

Further Device Embodiments

It will be appreciated that, while specific embodiments of a device are described above, many variations are possible in various embodiments.

In the above embodiments, the sample flows through the connecting conduit 20 by capillarity. However, the flow of the sample through the connecting conduit 20 may equally be driven by a pressure difference or by any other means.

The microfluidic liquid handling structure as described above may be implemented on a 'lab on a disc' cartridge designed for rotation about an axis of rotation. Once the sample has been introduced into the microfluidic liquid handling structure 10, through the sample inlet 16, the sample inlet is sealed and the device is placed in an instrument comprising a rotation mechanism. In this embodiment, the image capture device may be integral to the instrument into which the cartridge is placed. The rotation mechanism allows angular positioning of the cartridge to be controlled. A positioning sensor may be used to assist the precise alignment of the detection portion 24 with the field of view 26 of the image capture device 28. The cartridge may also be immobilized or slowly rotating for discrete positioning purposes and all fluidic functions may be accomplished by capillary based handling of the blood sample without further interference/assistance. Once the cells in the sample have been classified according to an embodiment as described above, the cartridge may be rotated about an axis of rotation for the further processing of the same or a different sample within the device. Upon rotation of the cartridge about the axis of rotation, a liquid sample in the cartridge experiences a centrifugal force. An example of such a cartridge can be found in application WO2013135713, incorporated herein by reference.

In some embodiments, associated with each cartridge is the value of $V_{FOV}$ for that particular cartridge for use where necessary in the methods described above. For example, $V_{FOV}$, may be recorded on a machine readable element on the cartridge or may be stored elsewhere.

All of the fluidic structures described herein may be designed in polar coordinates relative to said axis of rotation. Consequently, all structures may be characterized by their radial and angular dimensions and positioning in respect of an axis of rotation.

As mentioned above, in some embodiments, the microfluidic liquid handling structure is provided on a cartridge. The cartridge, in some embodiments, in particular those using a rotational mechanism, resembles a CD/DVD configuration constituted by two transparent and planar circular halves brought together by an intermediate adhesive layer. The halves are preferably engraved with the microfluidic structures and openings to the exterior described above. With precise alignment of the microfluidic structures, the three parts may be assembled and bonded to form a self-contained cartridge.

It will be appreciated that the dimensions of the connection conduit 20, including its preparation and detection portions, and those of the loading 12 and waste 14 chambers may be adjusted.

Although the embodiments described above are adapted for the processing of a blood sample, at least some of the above embodiments are suitable for processing any liquid sample, for example any liquid to be reacted with one or more reagents prior to imaging, in which objects are to be counted.

The shape and length of the connection conduit 20 may be arranged in such a manner that enables space saving within the microfluidic liquid handling structure, for example using a meandering configuration. The trajectory of the connection conduit 20 may be provided within a single plane of the microfluidic liquid handling structure. It will be appreciated that although a straight connection conduit 20 is depicted in FIG. 16A, any shape suitable for providing a substantially planar trajectory of the blood flow within the microfluidic liquid handling structure could be provided.

It will be appreciated that other known reagents and combinations thereof may be used in the device. It will also be appreciated that the reagents may be arranged to have different dimensions in the preparation portion 22.

The described processes can be implemented using any suitable stand-alone or distributed computing environment using any suitable computing platform or processor, for example an integrated circuit, self-contained or in combination with other components of the system, a dedicated computing device housed on an appropriate card together with the other components of the system or otherwise, a standalone computing device such as a personal computer, tablet computer or mobile phone or a server which performs the necessary processes at least in part remotely exchanging data over a network connection. The processing may be implemented in a client-server architecture, with the processing being distributed between the client and the server in any appropriate manner. The client may include any of the above mentioned devices.

While specific embodiments have been described above for illustration, many variations, alterations and juxtapositions of the specific features in addition to those specifically mentioned above, will occur to the skilled reader upon reading the description and are within the scope of the present disclosure. The scope of the invention is defined by the appended claims.

The invention claimed is:

1. A method of classifying blood cells in a blood sample, the method comprising:
    capturing a sequence of frames of the sample with an image capture device as the sample flows through a field of view of the image capture device;
    segmenting each frame into objects and background;
    tracking each segmented object over at least some of the frames;
    classifying the tracked objects in each of the respective at least some of the frames to obtain a classification result for each tracked object and each of the respective at least some of the frames; and computing an overall classification result for each tracked object based on the respective classification results from each of the at least some of the frames to classify each tracked object as one of a plurality of object types, wherein the object types include one or more cell types.

2. The method as claimed in claim 1, wherein computing an overall classification result includes averaging or calculating the median of the respective classification results over frames.

3. The method as claimed in claim 1, wherein computing an overall classification result includes applying one or more rules to a respective sequence of classification results computed from the respective at least some of the frames for each object.

4. The method as claimed in claim 1, wherein the classification result for each tracked object and each of the respective at least some of the frames is indicative of a respective likelihood of belonging to each of the object types.

5. The method as claimed in claim 4, wherein an object type of the plurality of object types has a non-isotropic characteristic feature and the method includes assigning a tracked object to that object type if a classification result for that tracked object belonging to that object type in a preset number of the respective at least some of the frames exceeds a threshold value or a change of classification result for that tracked object belonging to that object type between the respective at least some of the frames exceeds a threshold value.

6. The method as claimed in claim 1, the method comprising computing a respective proportion of the number of objects classified as each cell type out of the number objects classified as any one of the one or more cell types.

7. The method as claimed in claim 6, the method comprising estimating a count of objects of any one of the one or more cell types and computing a count of objects of each of the one or more cell types based on the estimated count of objects of any one of the one or more cell types and the respective proportions.

8. The method as claimed in claim 7, wherein estimating a count includes identifying objects of any of the one or more cell types in each frame;
selecting a plurality of frames of the sequence of frames and determining a frame cell count of identified objects in each selected frame; and
combining the determined frame cell counts to compute an estimated count of objects of any one of the one or more cell types.

9. The method as claimed in claim 8, wherein combining the determined frame cell counts includes fitting a distribution function to the determined frame cell counts and computing the estimated cell count based on the fitted distribution.

10. The method as claimed in claim 8, wherein frames are selected based on an estimate of cell velocity in one or more frames.

11. The method as claimed in claim 1, wherein the one or more cell types are leukocytes or leukocyte types.

12. The method as claimed in claim 11, wherein the one or more cell types include one or more of: neutrophil, basophil, eosinophil, lymphocyte and monocyte.

13. A system for estimating a cell count in a blood sample, the system comprising an image capture device having a field of view and an image processor, wherein the image processor is configured to:

capture a sequence of frames of the sample with an image capture device as the sample flows through a field of view of the image capture device;
segment each frame into objects and background;
track each segmented object over at least some of the frames;
classify the tracked objects in each of the respective at least some of the frames to obtain a classification result for each tracked object and each of the respective at least some of the frames; and
compute an overall classification result for each tracked object based on the respective classification results from each of the at least some of the frames to classify each tracked object as one of a plurality of object types, wherein the object types include one or more cell types.

14. The system as claimed in claim 13, wherein computing an overall classification result includes averaging or calculating the median of the respective classification results over frames.

15. The system as claimed in claim 13, wherein computing an overall classification result includes applying one or more rules to a respective sequence of classification results computed from the respective at least some of the frames for each object.

16. The system as claimed in claim 13, wherein the classification result for each tracked object and each of the respective at least some of the frames is indicative of a respective likelihood of belonging to each of the object types.

17. The system as claimed in claim 16, wherein an object type of the plurality of object types has a non-isotropic characteristic feature and the image processor is configured to assign a tracked object to that object type if a classification result for that tracked object belonging to that object type in a preset number of the respective at least some of the frames exceed a threshold value, or a change of classification result for that tracked object belonging to that object type between the respective at least some of the frames exceeds a threshold value.

18. The system as claimed in claim 13, the processor being configured to compute a respective proportion of the number of objects classified as each cell type out of the number objects classified as any one of the one or more cell types.

19. The system as claimed in claim 18, the process being configured to estimate a count of objects of any one of the one or more cell types and to compute a count of objects of each of the one or more cell types based on the estimated count of objects of any one of the one or more cell types and the respective proportions.

20. The system as claimed in claim 19, wherein estimating a count includes identifying objects of any of the one or more cell types in each frame;
selecting a plurality of frames of the sequence of frames and determining a frame count of identified objects in each selected frame; and
combining the determined frame counts to compute an estimated count of objects of any one of the one or more cell types.

21. The system as claimed in claim 13, wherein the one or more cell types are leukocytes or leukocyte types.

22. The system as claimed in claim 21, wherein the one or more cell types include one or more of: neutrophil, basophil, eosinophil, lymphocyte and monocyte.

* * * * *